United States Patent
Scalese et al.

[11] Patent Number: 6,092,924
[45] Date of Patent: Jul. 25, 2000

[54] MICROWAVE MOISTURE ANALYZER: APPARATUS AND METHOD

[75] Inventors: Robert F. Scalese, Superior; Thomas B. Taylor, Golden; Tim Holzschuh, Littleton; Douglas E. Harbert, Denver; Thomas G. Plaven, Littleton; Martin L. Maple, Aurora, all of Colo.; Jan Claesson, Granger, Ind.

[73] Assignee: Denver Instrument Company, Arvada, Colo.

[21] Appl. No.: 09/021,570

[22] Filed: Feb. 10, 1998

[51] Int. Cl.[7] .................................................. G01N 25/00
[52] U.S. Cl. ............................................ 374/14; 333/208
[58] Field of Search ................................. 374/14; 73/76; 333/209, 227, 228, 231; 331/176; 219/696, 708, 746, 750; 34/259

[56] References Cited

U.S. PATENT DOCUMENTS

| | | |
|---|---|---|
| Re. 32,861 | 2/1989 | Collins et al. . |
| Re. 34,373 | 9/1993 | Collins et al. . |
| 3,652,940 | 3/1972 | Reiter et al. ............................ 333/230 |
| 3,680,012 | 7/1972 | Moreau ................................... 333/209 |
| 3,748,605 | 7/1973 | Baynham et al. ....................... 333/209 |
| 3,758,737 | 9/1973 | Ironfield ................................. 333/209 |
| 3,869,681 | 3/1975 | Klein et al. ............................. 331/96 |
| 3,890,825 | 6/1975 | Davis . |
| 3,909,598 | 9/1975 | Collins et al. . |
| 3,916,670 | 11/1975 | Davis et al. . |
| 4,037,182 | 7/1977 | Burnett et al. .......................... 333/209 |
| 4,106,329 | 8/1978 | Takahashi et al. ....................... 374/14 |
| 4,127,834 | 11/1978 | Stringfellow et al. .................. 331/176 |
| 4,165,633 | 8/1979 | Raisanen . |
| 4,168,623 | 9/1979 | Thomas, Jr. . |
| 4,193,116 | 3/1980 | Funk . |
| 4,276,462 | 6/1981 | Risman . |
| 4,291,775 | 9/1981 | Collins . |
| 4,312,218 | 1/1982 | Eckles . |
| 4,316,384 | 2/1982 | Pommer et al. . |
| 4,390,768 | 6/1983 | Teich et al. . |
| 4,398,835 | 8/1983 | Athey et al. . |
| 4,413,168 | 11/1983 | Teich . |
| 4,438,500 | 3/1984 | Collins et al. . |
| 4,457,632 | 7/1984 | Collins et al. . |
| 4,485,284 | 11/1984 | Pakulis ................................... 374/14 |
| 4,521,746 | 6/1985 | Hwan et al. ............................ 331/96 |
| 4,554,132 | 11/1985 | Collins . |
| 4,565,669 | 1/1986 | Collins et al. . |
| 4,566,312 | 1/1986 | Collins et al. . |
| 4,566,804 | 1/1986 | Collins et al. . |

(List continued on next page.)

FOREIGN PATENT DOCUMENTS

| | | |
|---|---|---|
| 44-23956 | 10/1969 | Japan . |
| 403172746 | 7/1991 | Japan ..................................... 374/14 |

OTHER PUBLICATIONS

H.G. Wiedemann, Universal measuring instrument for gravimetric investigations under variable conditions, Mettler Instrumente AG, Stafa/ZH, Switzerland, Feb. 1969.

Frank Reggia, Magnetically Tunable Microwave Bandpass Filter, The Microwave Journal, Jan. 1963.

Okress, Ernest C., Microwave Power Engineering, Apr. 1968, pp. 49–53, 63, 156 and 195, vol. 2, Academic Press, New York and London.

Leonhardt, G.F., Et Al., Microwave Drying of Microorganisms. II. The Use of Microwave Oven for the Determination of Moisture Content of Pressed Yeast, Journal of Microwave Power, Feb. 1978, 4 pages total, vol. 13(3), IMPI, Canada.

Risman, P.O., A Microwave Applicator for Drying Food Samples, Journal of Microwave Power, Aug. 1978, cover page, pp. 298–301, vol. 13 (4), IMPI, Canada.

*Primary Examiner*—Adolf Deneke Berhane
*Assistant Examiner*—Pia Tibbits
*Attorney, Agent, or Firm*—Bernhard Kreten

[57] ABSTRACT

A toploading weighing apparatus which determines weight loss for a sample by drying the sample in a cylindrical microwave with a specific structure.

27 Claims, 30 Drawing Sheets

U.S. PATENT DOCUMENTS

| | | |
|---|---|---|
| 4,620,146 | 10/1986 | Ishikawa et al. . |
| 4,651,285 | 3/1987 | Collins et al. . |
| 4,681,996 | 7/1987 | Collins et al. . |
| 4,749,054 | 6/1988 | Virtanen et al. . |
| 4,750,143 | 6/1988 | Heitz et al. . |
| 4,753,889 | 6/1988 | Collins . |
| 4,835,354 | 5/1989 | Collins et al. . |
| 4,838,705 | 6/1989 | Byers, Jr. et al. . |
| 4,851,630 | 7/1989 | Smith . |
| 4,861,556 | 8/1989 | Neas et al. . |
| 4,882,286 | 11/1989 | Neas et al. . |
| 4,939,489 | 7/1990 | Gueble et al. ............. 333/227 |
| 4,946,797 | 8/1990 | Neas et al. . |
| 5,085,527 | 2/1992 | Gilbert ................ 374/14 |
| 5,176,146 | 1/1993 | Maurice et al. ............ 374/122 |
| 5,211,252 | 5/1993 | Henderson et al. . |
| 5,215,715 | 6/1993 | Haswell et al. . |
| 5,216,388 | 6/1993 | Dipoala ................. 331/96 |
| 5,256,978 | 10/1993 | Rose . |
| 5,318,754 | 6/1994 | Collins et al. . |
| 5,329,255 | 7/1994 | Hayes et al. ............ 331/176 |
| 5,397,993 | 3/1995 | Tews et al. . |
| 5,420,039 | 5/1995 | Renoe et al. . |
| 5,632,921 | 5/1997 | Risman et al. . |

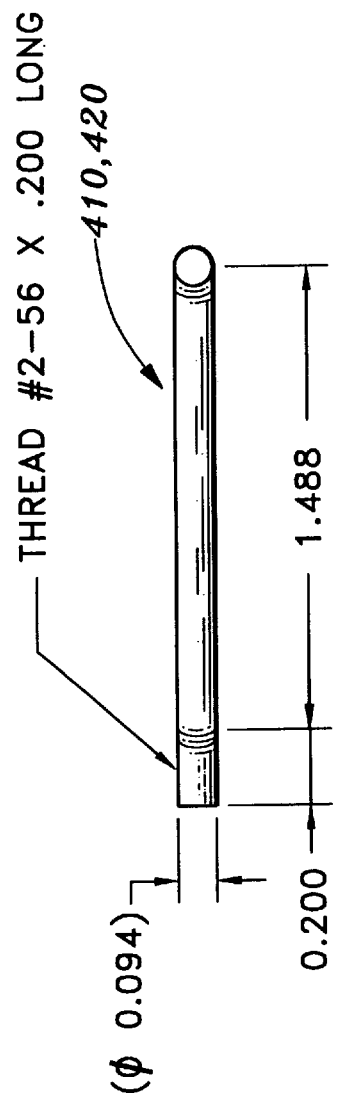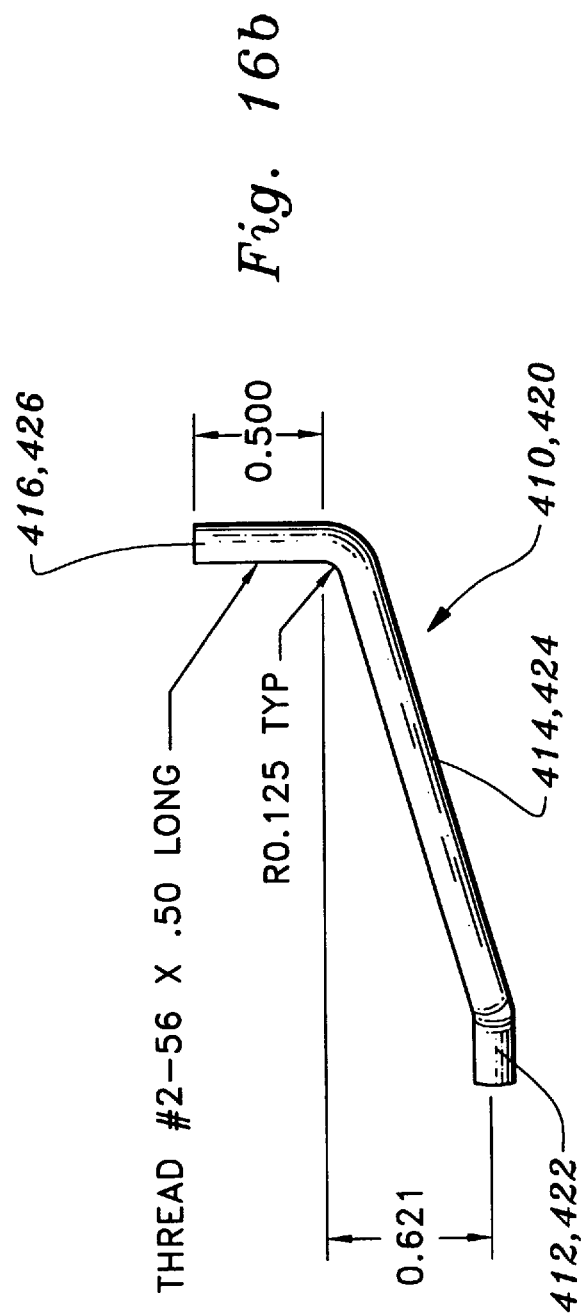
Fig. 16a
Fig. 16b

Fig. 20

| Fig. 20A | Fig. 20C |
|----------|----------|
| Fig. 20B | Fig. 20D |

Fig. 21

| Fig. 21A | Fig. 21C |
|----------|----------|
| Fig. 21B | Fig. 21D |

MICROWAVE MOISTURE ANALYZER: APPARATUS AND METHOD

FIELD OF THE INVENTION

The instant invention relates generally to a moisture analyzer and, in particular, to a microwave moisture analyzer for loss on drying applications.

BACKGROUND OF THE INVENTION

A multiplicity of devices and analytical methods have been developed in an attempt to obtain fast and accurate quantitative analysis of a vast array of products which are manufactured subject to strict control of moisture. For example, certain products have a specific range of moisture which dictates the taste and/or texture of the product. Thus, once the consumer associates a specific taste and/or texture to the product the uniformity of that taste and/or texture becomes a hallmark to the product's long term acceptance and ultimate success. Furthermore, moisture content is a specific process control in food processing, waste water treatment and materials processing.

Typically, these products require the volatilization of moisture or the like from the substance for moisture determination. In recent years, conventional microwave heating has been employed in the methods to remove various volatiles such as moisture followed by calculations of the amount of moisture lost. Conventional microwave heating requires the use of high power levels for providing effective drying due to the conventional microwave ovens employing random direction $T_e$ waves as the dominant energy field for the drying process. As a result, these microwave ovens produce hot and cold spots, over heating edges and charring of the products being analyzed. The traditional attempts to avoid these problems was to use a mechanical device (e.g., a turntable) to move the sample in relationship to the cavity during heating or to use a mechanical stirrer to continually alter the mode pattern of the waves within the cavity. Even though these attempts were improvements to the conventional microwave oven, they failed to provide a satisfactory solution which provided fast and accurate moisture determination of the product without the degradation of the product due to these problems.

Thus, there continues to be a need for an efficient microwave moisture analyzer which offers uniformity of microwave heating and rapid moisture determining analysis. This is particularly important in light of the fact that most of the testing of products is related to process control in some form or another. Thus, the speed of the analysis and tests are hallmarks of high quality mass production. In addition, there is a need for a microwave moisture analyzer which provides timely feedback for maintaining tight tolerances of both the process and product produced thereby. Furthermore, a microwave moisture analyzer is needed which includes automated functions which simplify routine analysis thereby substantially eliminating the dependency of the result of the analysis on the skill and care exercised by the operator.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 3,909,598 | September 30, 1975 | Collins, et al. |
| 4,106,329 | August 15, 1978 | Takahashi, et al. |
| 4,165,633 | August 28, 1979 | Raisanen |
| 4,168,623 | September 25, 1979 | Thomas, Jr. |
| 4,193,116 | March 11, 1980 | Funk |
| 4,276,462 | June 30, 1981 | Risman |
| 4,291,775 | September 29, 1981 | Collins |
| 4,312,218 | January 26, 1982 | Eckles |
| 4,316,384 | February 23, 1982 | Pommer, et al. |
| 4,390,768 | June 28, 1983 | Teich, et al. |
| 4,398,835 | August 16, 1983 | Athey, et al. |
| 4,413,168 | November 1, 1983 | Teich |
| 4,438,500 | March 20, 1984 | Collins, et al. |
| 4,457,632 | July 3, 1984 | Collins, et al. |
| 4,554,132 | November 19, 1985 | Collins |
| 4,565,669 | January 21, 1986 | Collins, et al. |
| 4,566,312 | January 28, 1986 | Collins, et al. |
| 4,566,804 | January 28, 1986 | Collins, et al. |
| 4,651,285 | March 17, 1987 | Collins, et al. |
| 4,681,996 | July 21, 1987 | Collins, et al. |
| 4,749,054 | June 7, 1988 | Virtanen, et al. |
| 4,750,143 | June 7, 1988 | Heitz, et al. |
| 4,753,889 | June 28, 1988 | Collins |
| Re. 32,861 | February 7, 1989 | Collins, et al. |
| 4,835,354 | May 30, 1989 | Collins, et al. |
| 4,838,705 | June 13, 1989 | Byers, Jr. et al. |
| 4,861,556 | August 29, 1989 | Neas, et al. |
| 4,882,286 | November 21, 1989 | Neas, et al. |
| 4,946,797 | August 7, 1990 | Neas, et al. |
| 5,211,252 | May 18, 1993 | Henderson, et al. |
| 5,215,715 | June 1, 1993 | Haswell, et al. |
| Re. 34,373 | September 7, 1993 | Collins, et al. |
| 5,318,754 | June 7, 1994 | Collins, et al. |
| 5,420,039 | May 30, 1995 | Renoe, et al. |
| 5,632,921 | May 27, 1997 | Risman, et al. |

SUMMARY OF THE INVENTION

The instant invention is distinguished over the known prior art in a multiplicity of ways. For one thing, the instant invention provides a microwave moisture analyzer for loss on drying applications which provides fast and accurate quantitative analysis of a vast array of products which are manufactured subject to strict control of moisture. In addition, the microwave moisture analyzer according to the instant invention provides fast and uniform drying of product samples for real-time process control without degradation of the samples due to charring thereby providing, inter alia, timely feedback for maintaining tight tolerances of a mass produced product. Furthermore, the instant invention includes automated functions which simplify routine analysis thereby substantially eliminating the dependency of the result of the analysis on the skill and care exercised by the operator.

In a preferred form, the microwave moisture analyzer of the instant invention includes a power supply, a magnetron, a power module operatively coupled between said power supply and said magnetron for driving said magnetron, a wave guide communicating with the magnetron and with a microwave containment chamber for delivering energy thereto, and a precision electronic balance operatively disposed within the microwave chamber and allowing a specimen being assayed to be continuously weighed while powering the microwave to dry the specimen. In addition, a ventilation chamber is provided for venting moisture from the microwave during at least a first wave of drying time. A processing unit and associated memory allows means for data acquisition, processing and storage of data from both the power module driving the magnetron and the electronic balance while continuously weighing the specimen for loss on drying moisture analysis.

The microwave containment chamber is partitioned into a lower chamber and an upper chamber wherein the upper chamber is pivotably coupled to said lower chamber such that said upper chamber can move from a closed substantially horizontal position to an opened upright position for toploading of a specimen faster. The upper and lower chamber when in a closed position define an internal cavity having a base, cylindrical sidewalls extending from said base and operatively coupled thereto and a perforated top wall wherein moisture can be aspirated therethrough without allowing microwave leakage. The base of the cylindrical chamber includes a pair of portals disposed approximately ninety degrees apart such that the energy delivered from the magnetron can be guided to the portals via a bifurcated wave guide for delivering energy within the cylindrical cavity of the microwave containment chamber.

In addition, a pair of tuning rods are disposed within the interior of the containment chamber at a location above the portals. The tuning rods are used to set-up the microwave mode entering the chamber into a resonance condition. Specifically, the tuning rods set-up two resonances such that they interact with one another to create a magnetic stirring without the use of a mechanical stirrer. Preferably, the tuning rods traverse a median of the portals.

Furthermore, an attenuator is provider within one of the two bifurcated members of the wave guide communicating energy between the magnetron and the microwave chamber. The tuning stub is used to attenuate a third mode of energy within a wave guide to increase the efficiency of the dual mode wave guide field creating a cylindrical stirring effect.

OBJECTS OF THE INVENTION

Accordingly, a primary object of the instant invention is to provide a new, novel and useful microwave moisture analyzer apparatus and method for loss on drying applications.

A further object of the instant invention is to provide a self contained, programmable moisture analyzer apparatus with microwave radiation and automatic determination of weight loss, suitable for non-flammable and non-toxic samples.

Another further object of the instant invention is to provide the apparatus and method as characterized above in which samples are heated using microwave energy to liberate moisture or other volatiles while continuously weighing the sample with an integral precision electronic balance until endpoint conditions are met.

Another further object of the instant invention is to provide the apparatus and method as characterized above which uses a high percentage of $T_m$ waves for allowing a lower power usage relative to conventional microwaves.

Another further object of the instant invention is to provide the apparatus and method as characterized above which includes a tuned wave guide and a tuned cylindrical induction microwave chamber.

Another further object of the instant invention is to provide the apparatus and method as characterized above which substantially reduces drying time compared with known methodologies.

Another further object of the instant invention is to provide the apparatus and method as characterized above which substantially reduces drying time without degradation of samples due to, inter alia, a reduced cavity size (e.g. 10% of a conventional oven cavity) of a microwave containment chamber thereby resulting in a favorable filling factor, i.e., the sample size divided by the cavity volume.

Another further object of the instant invention is to provide the apparatus and method as characterized above which is fast, accurate and easy to use.

Another further object of the instant invention is to provide the apparatus and method as characterized above which automatically calculates loss on drying moisture determination and documents the analysis on, inter alia, an internal printer and a video graphics array (VGA) display for providing good lab practice (GLP) and ISO support.

Another further object of the instant invention is to provide the apparatus and method as characterized above which allows setup by merely selecting an appropriate routine from a menu-driven software displayed on a backlit LCD display.

Another further object of the instant invention is to provide the apparatus and method as characterized above which allows the user to enter drying parameters by entering them through a keypad either by touching a corresponding number or entering the exact value with numeric keys.

Another further object of the instant invention is to provide the apparatus and method as characterized above which provides a development screen which conveniently illustrates the drying parameters including units, a plurality of temperatures and end-point selection for defining drying procedures.

Another further object of the instant invention is to provide the apparatus and method as characterized above which allows the drying procedures to be stored in the memory for later recall via meaningful alphanumeric program names.

Another further object of the instant invention is to provide the apparatus and method as characterized above which allows one key actuation of a drying procedure which has been established and recalled from memory with meaningful alphanumeric program names.

Another further object of the instant invention is to provide the apparatus and method as characterized above which provides easy operator ergonomics and cleaning via top entry of samples.

Another further object of the instant invention is to provide the apparatus and method as characterized above which provides meaningful recall from memory/data acquisition and graphical/plotting displays.

Viewed from a first vantage point, it is an object of the present invention to provide a loss on drying apparatus, comprising in combination: weighing means operatively disposed within a cylindrical microwave.

Viewed from a second vantage point, it is an object of the present invention to provide a method for loss on drying, the steps including: placing a specimen in a cylindrical microwave; continuously weighing the specimen while powering the microwave to dry the specimen; venting moisture from the microwave during a first wave of drying, and sampling the weight change periodically.

Viewed from a third vantage point, it is an object of the present invention to provide a microwave moisture analyzer; comprising in combination: a microwave containment chamber including a bottom wall, a top wall and a substantially cylindrical side wall extending between and connected to both said top and bottom walls; the bottom wall including a pair of portals disposed therein; a microwave energy source; a wave guide operatively coupled between the microwave energy source and the portals for delivering microwave energy to the chamber; means for weighing a sample to be assayed; the weighing means operatively extending through the bottom wall and into the chamber for supporting the sample to be assayed; means for controlling the delivery of microwave energy to the chamber as a function of the sample being microwaved until a sample is dried; means operatively coupled to the weighing means for automatically determining loss on drying moisture determination.

These and other objects will be made manifest when considering the following detailed specification when taken in conjunction with the appended drawing figures.

BRIEF DESCRIPTION OF THE DRAWINGS

FIG. 16a is a detailed front plan view of a tuning rod according to the instant invention.

FIG. 16b is a detailed side plan view of a tuning rod according to the instant invention.

DESCRIPTION OF PREFERRED EMBODIMENTS

Figure 1:
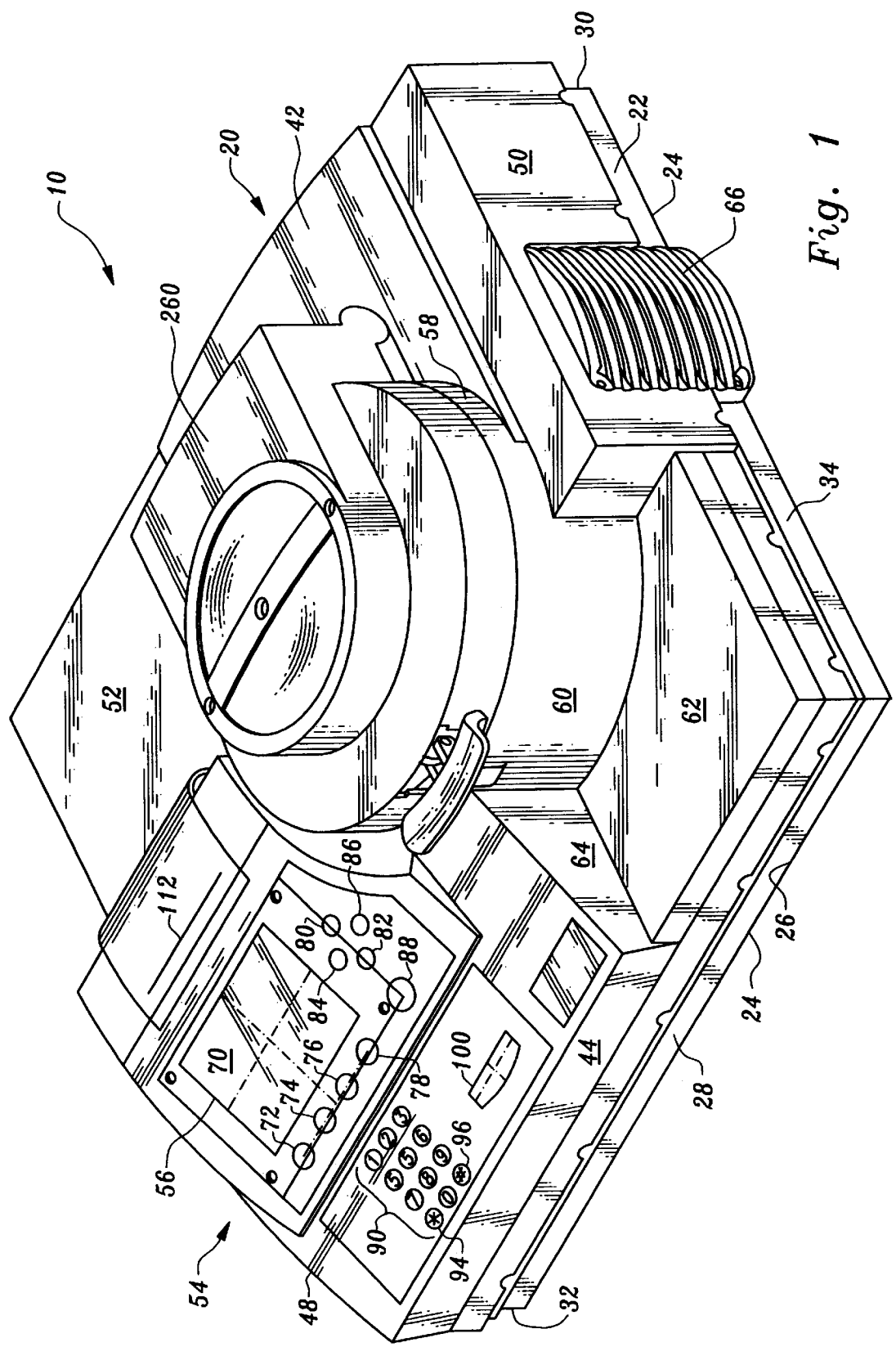
FIG. 1 is an elevational view from a front and side of the microwave moisture analyzer apparatus.

Considering the drawings, wherein like reference numerals denote like parts throughout the various drawing figures, reference numeral 10 is directed to the microwave moisture analyzer apparatus according to the instant invention.

Figure 2:
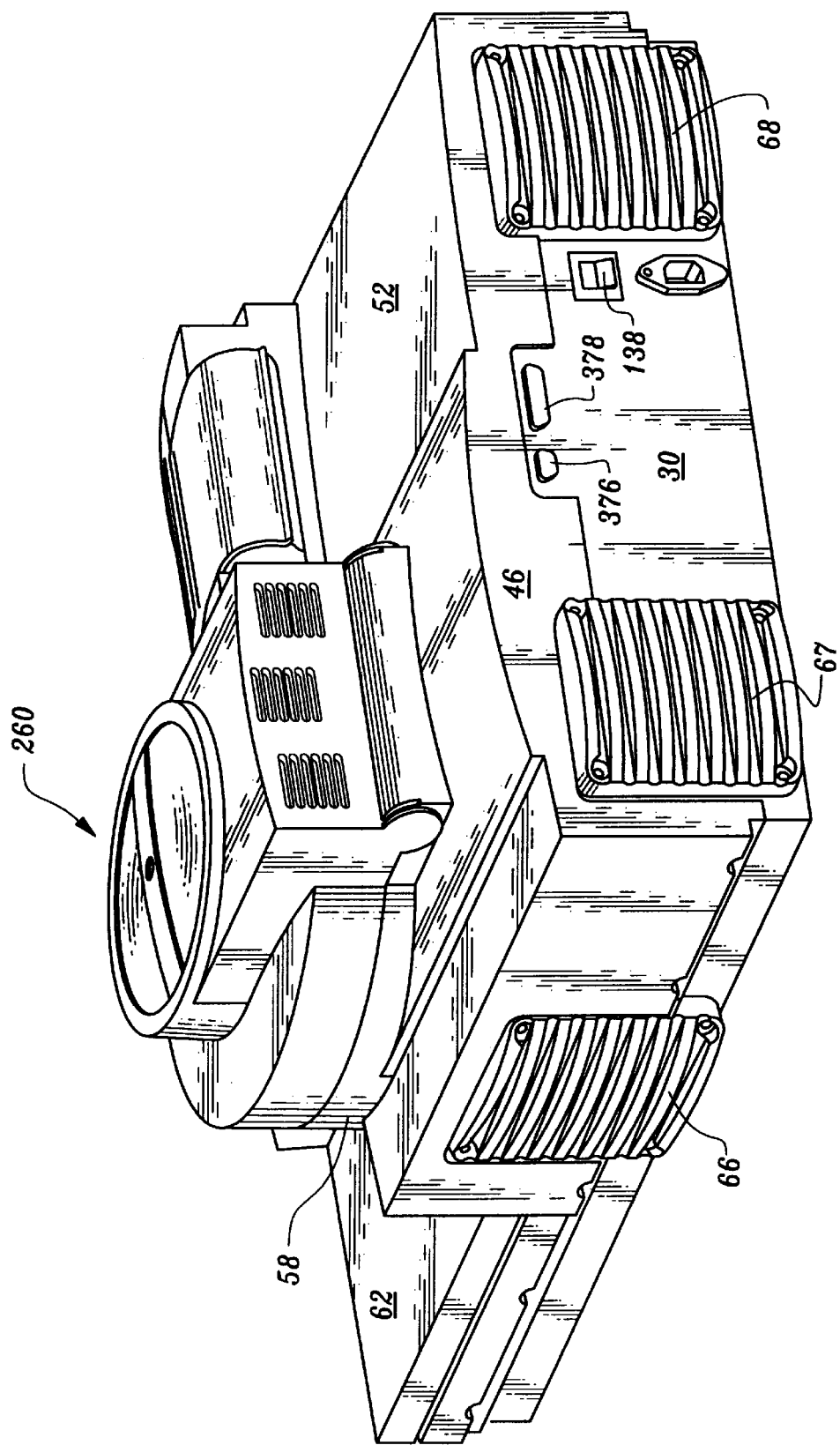
FIG. 2 is an elevational view from a side and rear of the apparatus.

In its essence and referring to FIGS. 1 and 2, the apparatus 10 according to the instant invention includes an enclosure 20 which includes a lower housing 22 and an upper housing 42. The lower housing 22 includes a planar bottom surface 24 having an outer periphery 26 with upwardly extending walls 28, 30, 32, 34 integrally formed with the periphery, thereby defining an open top box (please see FIG. 5). The open top box includes a plurality of partitioned areas which sequester different parts of the apparatus 10 into sectors. For example, one sector is an area where a power supply 120 is located and includes a ventilation means including a fan 152 passing through one of the side walls 30 to preclude adverse thermal excursions. Similarly, a second sector is provided which circumscribes a magnetron 170 and is similarly equipped with ventilation by means of a fan 176 to prevent unwanted temperature build-up and extend the life of the magnetron. A third sector is where an integral precision electronic balance 240 is housed and which communicates with the magnetron 170 via a bifurcated wave guide 200. The wave guide 200 communicates with a base 262 of a analysis chamber 260 which includes first and second portals 264, 266 and a centralized bore 270 in which a weighing rod 242 passes therethrough. The wave guide 200 substantially divides in quadrature, 90 degrees offset branches 204, 206 and portals 264, 266 from the base plate 262 extend upwardly to provide radiation to the sample being assayed and subsequently manipulated for a loss on drying analysis. Each of the partitioned areas are independently accessible depending on requisite need. Whether it be for maintenance or subsequent utilization in its intended working environment. The area above the balance 240 and where the microwave power is outputted includes a hinged and spring lift covered microwave analysis chamber 260 (please see FIG. 8). An interior of a hinged cover defines an upper chamber 300 and the cover includes a vent means defined by multiple fenestrations 311 located on a top plate 312 (FIG. 11) associated therewith and circulatory means to remove moisture during a loss on drying analysis. The hinged cover 300 protects the user by a plurality of micro-switches which disables the magnetron 170 should the cover 300 be opened while the apparatus 10 is in operation or if the cover 300 is improperly closed.

More specifically and referring to FIGS. 1 and 2, the upper housing 42 includes a top surface 52 and a circumscribing well 58 for receiving the analysis chamber 260. The top surface 52 of the upper housing 42 includes a user access area 54 for allowing a user to have access to a display 70, a plurality of soft keys 72, 74, 76, 78, direction keys 80, 82, 84, 86, an enter key 88, a numeric keypad 90 and a start key 100 and a printer slot 112 for receiving printed output. This area is downwardly sloped so that the user may easily view the display 70 and operate the plurality of keys before, during and after assaying the sample. The keys are surface mounted to protect against spillage. The display 70 is viewed through a display window 56 disposed in the top surface 52 of the upper housing 42. Preferably, there are four soft keys 72, 74, 76, 78 which are disposed directly under the display 70. In addition, the direction keys 80, 82, 84 and 86 are disposed through the top surface 52 of the upper housing 42 in a cruciform configuration. The enter key 88 is located to the right of the display 70 and below the directional keys. The numeric keypad 90 is disposed through the top surface 52 of the upper housing 42 at a location beneath both the display and the plurality of soft keys. The numeric keypad 90 includes ten numeric keys and a decimal and asterisk key 94, 96 allocated in four rows of three keys each thereby defining a 4 by 3 matrix. Furthermore, an oversized start key 100 is located to the right of the 4 by 3 matrix of keys 90.

The circumscribing well 58 of the upper housing 42 receives the analysis chamber 260. The upper housing 42 includes an integrally formed horizontally disposed planar work surface 62 located at the front right hand corner of the upper housing 42. The work surface 62 is formed at a lower elevation than the sloped user access area 54 and the upper chamber 300 of microwave analysis chamber 260 and can be employed as, inter alia, an area where a sample is placed between two quartz (glass) pads and/or plastic pans which are both microwave transparent. The work surface 62 transitions into a substantially planar vertically extending sidewall 64 and a front circular wall 60 of the circumscribing well 58 receiving the analysis chamber 260. In addition, the upper housing 42 includes an outer periphery with downwardly extending side walls 44, 46, 48, 50. The downwardly extending side wall 50 that defines the right side of the upper housing 42 includes an opening covered by a first air grill 66. In addition, the upper housing 42 is provided with a pair of spaced apart openings disposed in a back wall 46 for receiving a second and third air grill 67, 68 which communicate with a fan 152 cooling the electronics and power supply and the fan 176 providing temperature stability of the magnetron 170. The right side grill 66 allows air to enter through perforations 33 disposed in side wall 34 and then into the magnetron sector, over the magnetron 170 and then out through the fan 176 disposed on the back wall 30 of the lower housing 22 and back into the environment for providing cooling of the magnetron 170.

Figure 3:
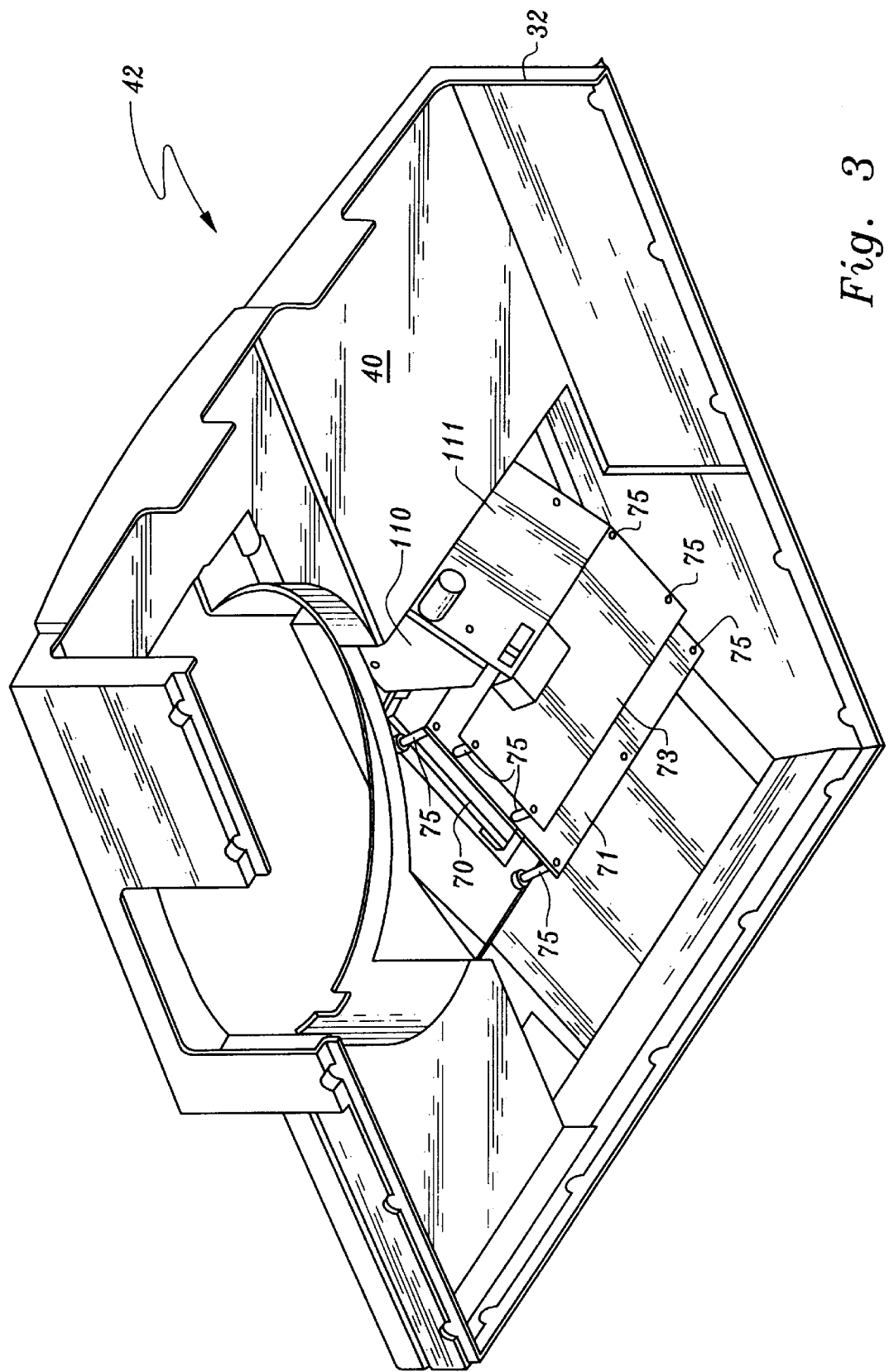
FIG. 3 is an elevational view of an underside of an upper housing according to the instant invention.

Referring to FIG. 3, an underside 40 of the upper housing 42 is shown. The underside of the upper housing 42 supports the display 70, a digital board 71 and a display driver board 73 for dividing the display 70. A plurality of stand-offs 75 are used as known in the art to connect the display 70, the digital board 71 and the driver board 73 in a parallel spaced apart relationship with respect to one another. In addition, the underside of the cover supports the printer 110 which is preferably a two hundred fifty six dot wide thermal graphics printer and a printer controller board 111 which are shown to be disposed above the display 70.

Figure 4:
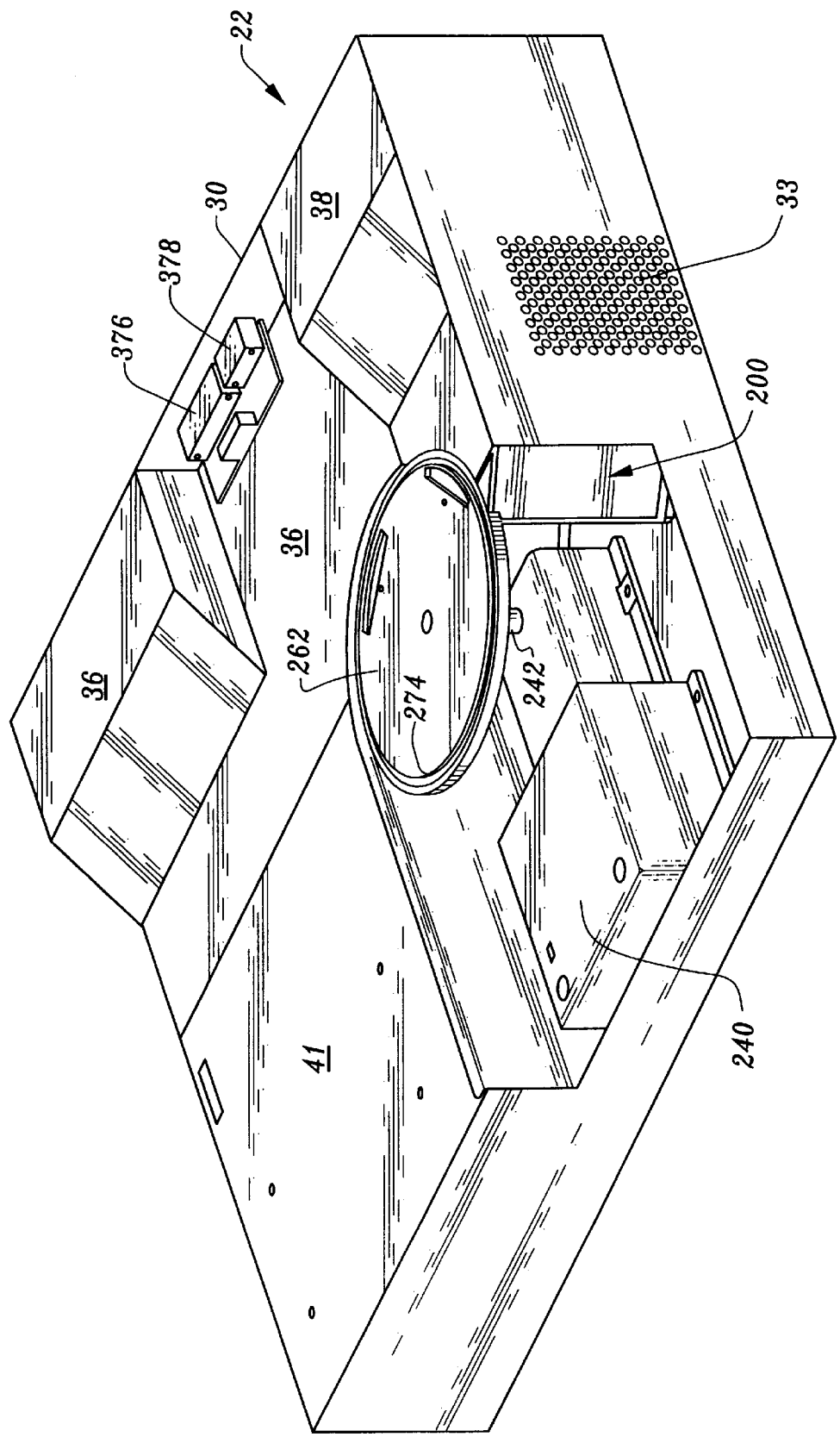
FIG. 4 is an elevational view from a front and side of the apparatus with the upper housing removed.

Referring to FIG. 4, the electronic balance 240 is shown disposed in a right front sector of the apparatus 10. The electronic balance 240 communicates with the base 262 of the analysis chamber 260 via a weighing rod 242 and the base 262 is directly coupled to the quadrature wave guide 200. In addition, a plurality of fan covers 36, 38 and an electronics protecting cover 41 precludes access to the components therebelow when the upper housing 42 is removed from the lower housing 22. Furthermore, a plurality of serial communication ports 376, 378 are disposed in the back wall 30 of the lower housing 22 and interposed between the fans covers 36, 38.

Figure 5:
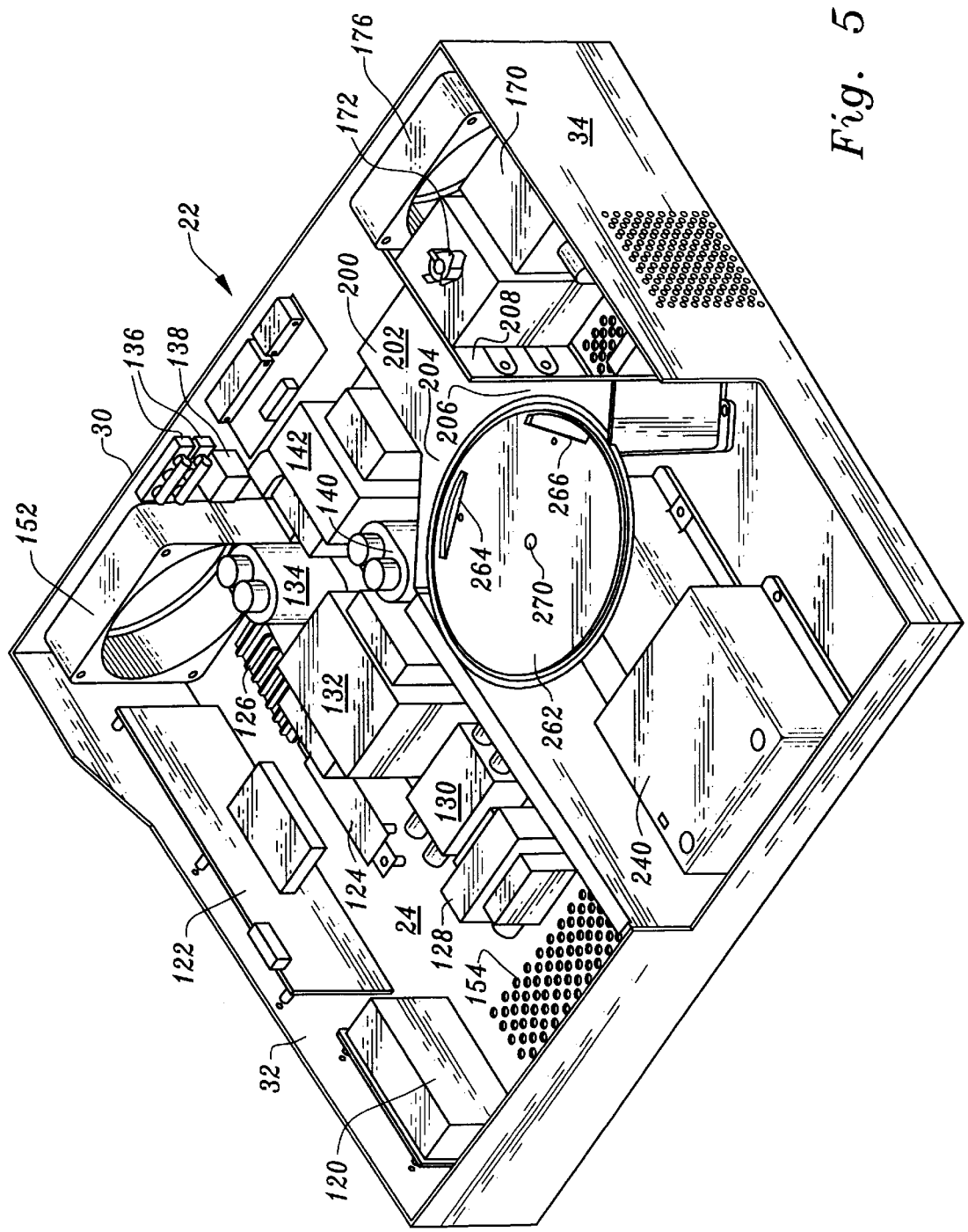
FIG. 5 is a front side elevational view of the apparatus with the upper housing and cover plates removed.

Referring to FIG. 5, the lower housing 22 is shown with the upper housing 42 and covers 36, 38, and 41 removed therefrom thereby defining the open top box structure. The power supply fan 152 is disposed on the back wall 30 of the first sector to provide ventilation for the components located therein. The first sector also includes a fuse block 136 for holding the fuses shown in FIGS. 20 and 21 and a power or on/off switch 138 which are disposed in the back wall 30 of the lower housing 22. In addition, the first sector includes a filament transformer 142, a capacitor 134, a back up capacitor 140, a terminal block 126, an anode transformer 132, a resistor bar 124, a filter 130, an isolation transformer 128, a power supply 120 and a power supply module or board 122. Preferably, the power supply module 122 and the power supply 120 are mounted on a side wall 32 of the lower housing 22, specifically, the left side wall 32 when viewing from the front of the apparatus 10 as per FIG. 1. The filament transformer 142, capacitor 134, back-up capacitor 140, anode transformer 132, filter 130 and isolation transformer 128 are spaced apart from the power board 122 and power supply 120 on an opposite side of the first sector. Interposed therebetween and coupled to bottom surface 24 is the resistor bar 124 and terminal block 126. Thus, the ventilation fan 152 receives air from a perforated opening 154 disposed in surface 24 towards the front of the first sector and induces air to flow over the components and through the fan 152 into the environment without the heat removal being impeded by the components contained therein.

Figure 22:
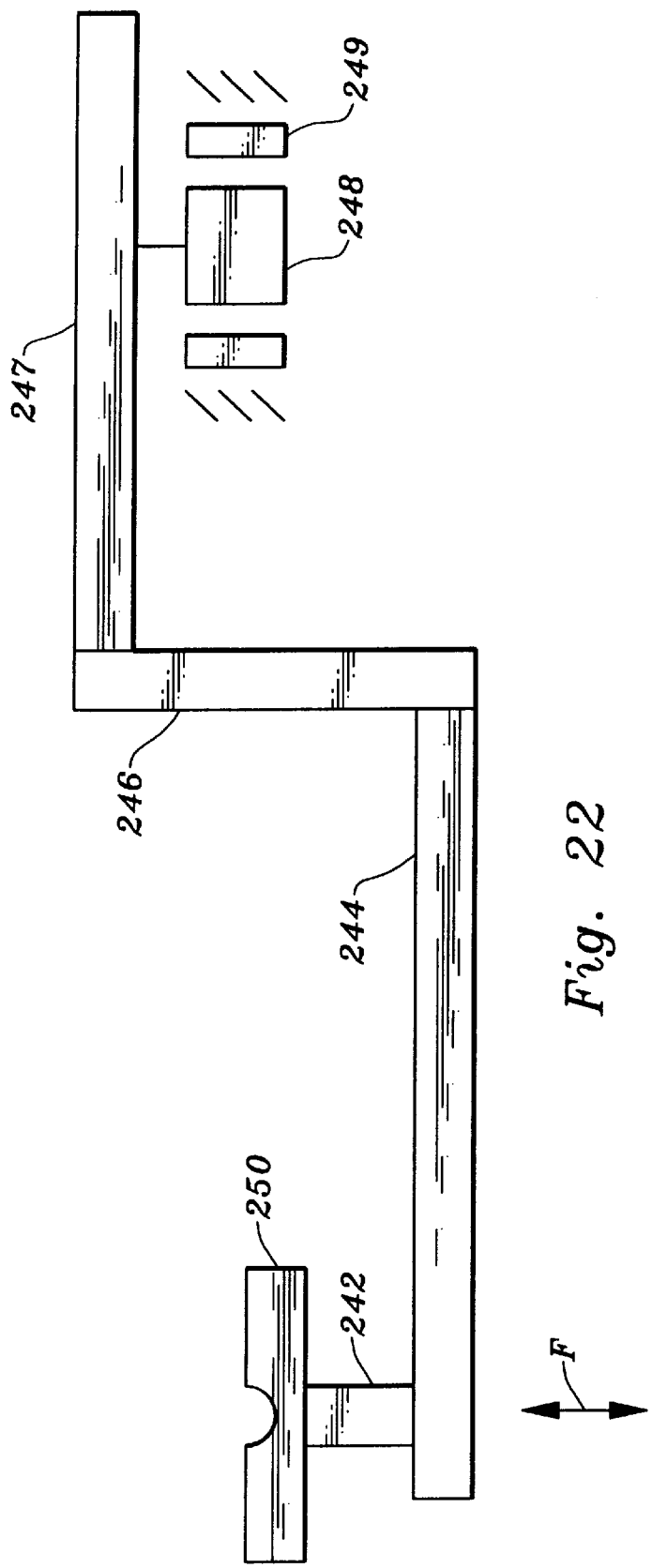
FIG. 22 is a block diagram of a balance according to the instant invention.

Referring to FIGS. 5 and 22, the second sector includes the integral electronic balance 240 which communicates with a carriage 250 holding the sample to be assayed by way of a weighing rod 242. The weighing rod 242 extends through the centralized bore 270 of the base 262 of the analysis chamber 260 and is connected to a substantially horizontal lever arm 244 of the balance 240. The lever arm 244 of the balance is operatively coupled to a vertically extending arm 246 which in turn is operatively coupled to a beam 247 connected to a coil 248 circumscribed by a winding 249. Thus, weight disposed on the pan will cause motion along the arrow F that displaces the coil 248 which is disposed in a field wherein the displacement of the coil 248 can be translated into a current or voltage correlative to the sample weight disposed on the pan. This type of electronic balance is known in the art as a toploading electronic balance. The balance 240 in combination with the top loading microwave chamber 260 allows a sample to be loaded into the chamber 260 and onto the carriage 250 coupled to the weighing rod 242 without damaging or breaking flexural bearing springs of the balance. In addition, the balance is guarded against vibration and electrical noise effects of the magnetron.

The third sector of the lower housing 22 includes the magnetron fan 176 disposed in the back wall 30 of the lower housing 22, the magnetron 170, a thermal switch 172 and the quadrature wave guide 200. Air enters through perforations 33 on right side wall 34 of the lower housing 22 and flows over the magnetron 170 through the fan 176 and back into the environment via fan operation. The thermal switch 172 is coupled to the main power supply 120 to provide protection so that the magnetron is shut off if excessive temperatures are reached. The magnetron 170 couples to a side 208 (FIG. 5) of a base 202 of a substantially Y shaped wave guide 200. The base 202 of the wave guide 200 bifurcates into the first wave guide channel 204 and the second wave guide channel 206. The first and second wave guide channels 204, 206 both communicate with the canoe shaped openings or portals 264, 266 disposed in the base 262 of the analysis chamber 260 such that radiation is emitted therethrough.

Figure 6:
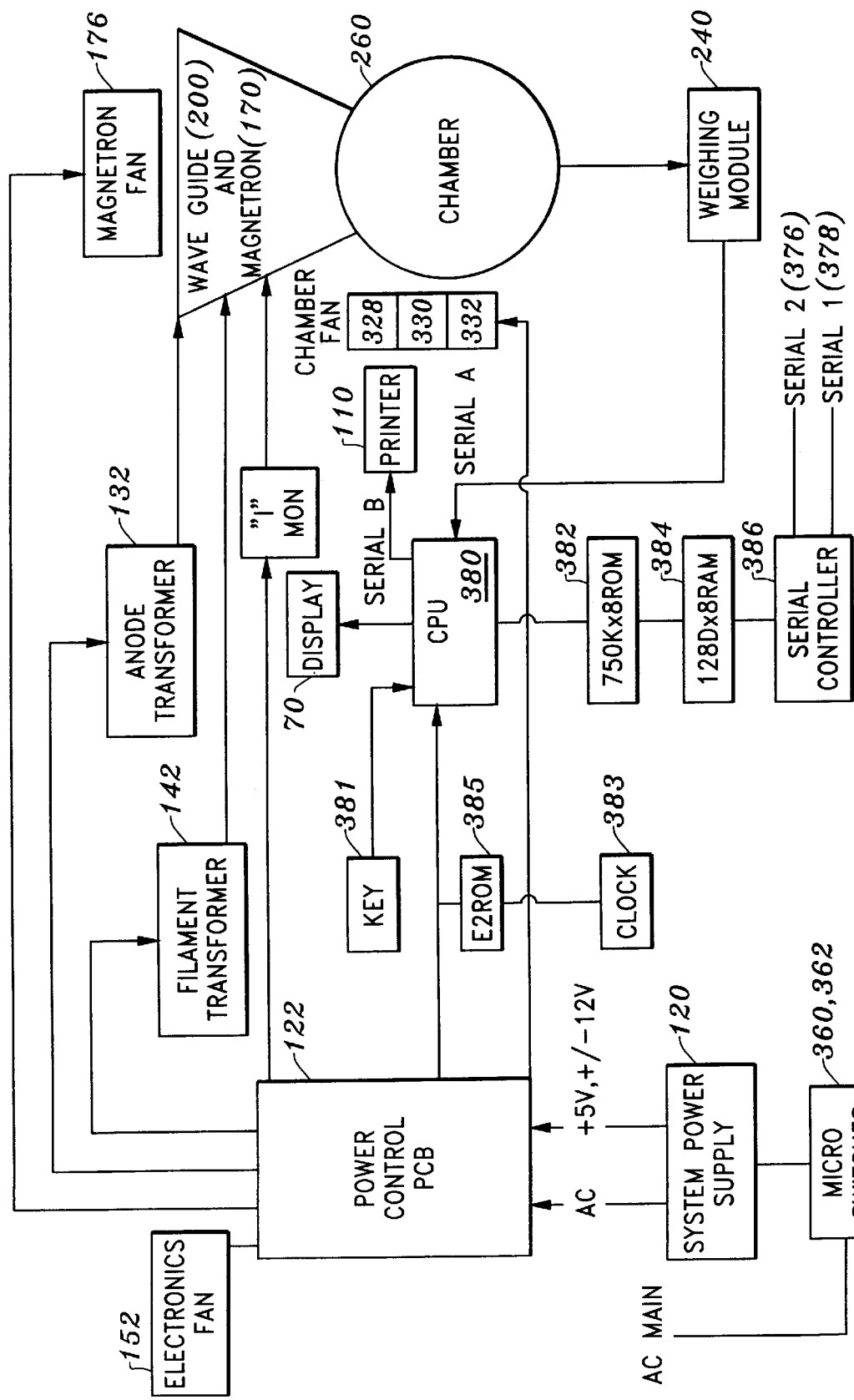
FIG. 6 is a system schematic of the apparatus according to the instant invention.

Referring to FIG. 6, a system schematic is shown of the apparatus according to the instant invention. The system includes a central processing unit 380 operatively coupled to a read only memory (ROM) 382, a random access memory (RAM) 384 and a serial controller 386 thereby allowing means for data acquisition, processing and storage. In addition, the serial controller 386 is operatively coupled to the serial ports 376, 378 for allowing bi-directional communication between the central processor 380 and an external computer or peripheral. In addition, the central processor 380 is operatively coupled to keys 381 which include the soft keys 72, 74, 76, and 78, direction keys 80, 82, 84 and 86, enter key 88, numeric keypad 90 and start key 100 disposed on the top surface 52 of the upper housing 42. In addition, the central processor 380 is operatively coupled to the display 70 and to the printer 110 for providing the display of information on the display 70 and a hard copy readout of information via the printer 110. Furthermore, an electrically erasable read-only memory 385 is operatively coupled between the power control board 122 and the central processing unit 380 for providing, inter alia, preprogrammed LOD (loss on drying) routines. Clock 383 provides the timing for memory 385.

The central processing unit 380 receives data from the balance or weighing module 240 and the power control module or board 122. The power control module 122 is operatively coupled to the system power supply 120 and is directly interrupted by at least one of the micro-switches 360 and 362 located on the lower chamber 280 of the microwave containment chamber 260. The power control board 122 is operatively coupled to an anode transformer 132 and the filament transformer 142 which are in turn connected to the magnetron 170 disposed on the wave guide 200. In addition, the power control board is operatively coupled to the magnetron fan 176 for controlling the temperature of the environment in which the magnetron 170 is disposed. The details of the power control board, the filament transformer 142, the anode transformer 132 and the magnetron 170 will be described infra.

The central processing unit 380 receives signals from the balance 240 which are indicative of the continuous weighing of the sample being assayed within the microwave analysis chamber 260. Thus, the central processing unit 380 receives signals from both the power control module 122 and the balance 240 which are indicative of the power being supplied to the magnetron 170 and thus the microwave analysis chamber 260 while assaying the sample and also the continuous weight of the sample before, during and after assaying of the sample.

Figure 7:
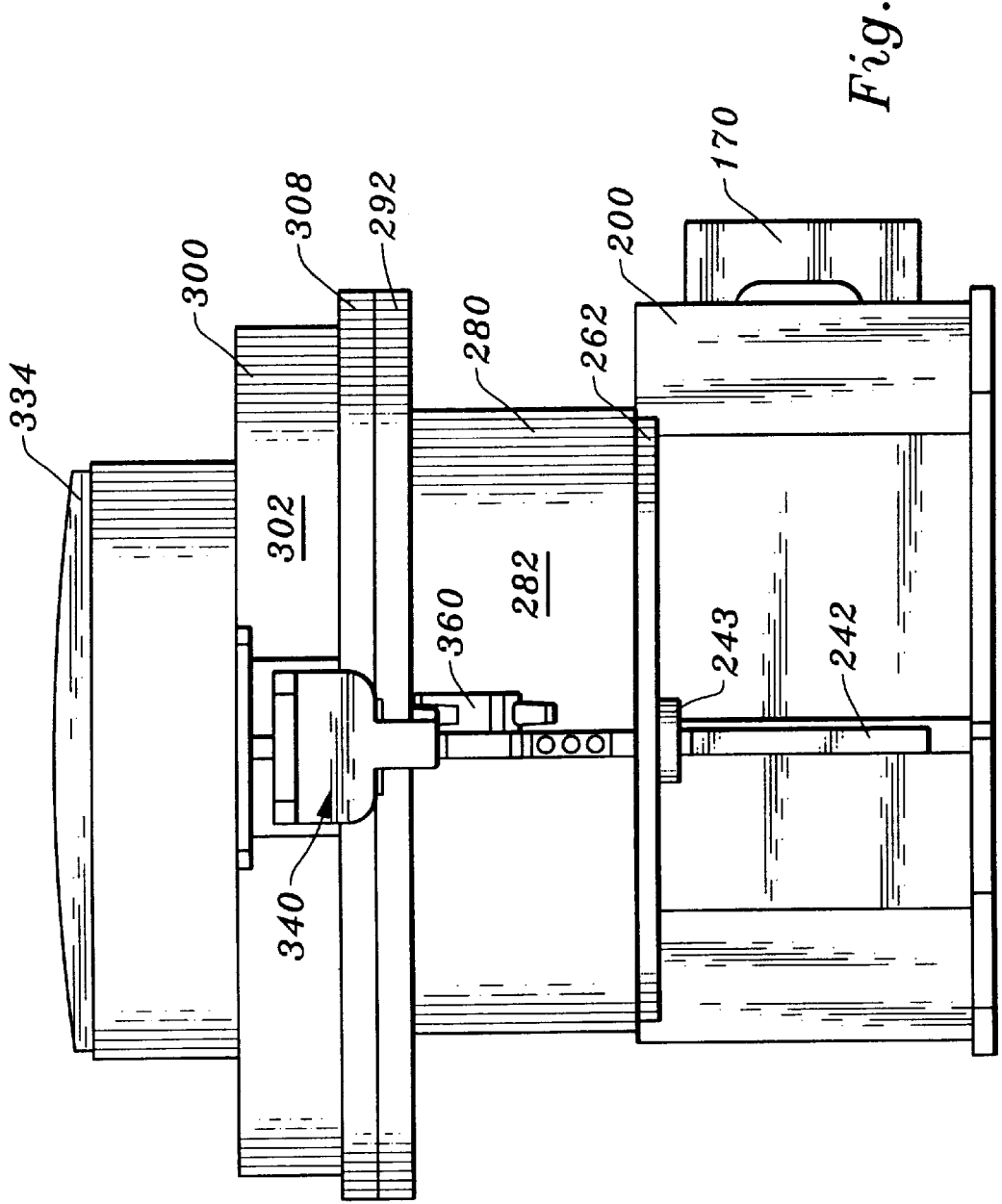
FIG. 7 is a front plan view of a microwave containment and analysis chamber and a wave guide.

Referring to FIG. 7, a front plan view of the microwave analysis chamber 260 is shown operatively coupled to both the weighing rod 242 of the balance 240 and the wave guide 200 interposed between the microwave analysis chamber 260 and the magnetron 170. Note the analysis chamber 260 is formed from a material which contains microwaves therewithin. The weighing rod 242 passes through a collar 243 prior to extending into the chamber 260 via the centralized bore 270. The microwave analysis chamber 260 is partitioned into the lower chamber 280 and the upper chamber 300. The lower chamber 280 includes the base 262 having an outer peripheral annular groove 274 (see FIG. 4) coupling to a side wall 282 having an interior cylindrical side wall 286 (see FIG. 13) vertically extending upwards to a lower sealing flange 292 (FIG. 7). The upper chamber 300 has a complemental sealing flange 308 including the choke which defines the partition between the upper and lower chambers 300, 280 respectively. The upper sealing flange 308 transitions into a cylindrical wall 302 also having an interior cylindrical side wall 306 defining a partitioned cylindrical microwave cavity of the containment chamber 260 along with the lower interior cylindrical wall 286. The upper cylindrical wall 302 transitions into a moisture evacuation compartment via the perforations 311 on top 312 which is covered by a lid 334 (FIG. 7). The upper chamber 300 is coupled to the lower chamber 280 via a latch means 340 which interacts with at least one micro-switch 360 which is directly coupled to the main power supply 120 delivering power to the magnetron 170 wherein the power supply 120 is inoperative when at least the one micro-switch 360 is in an opened positioned thereby disallowing false starts of the magnetron 170.

Figure 8:
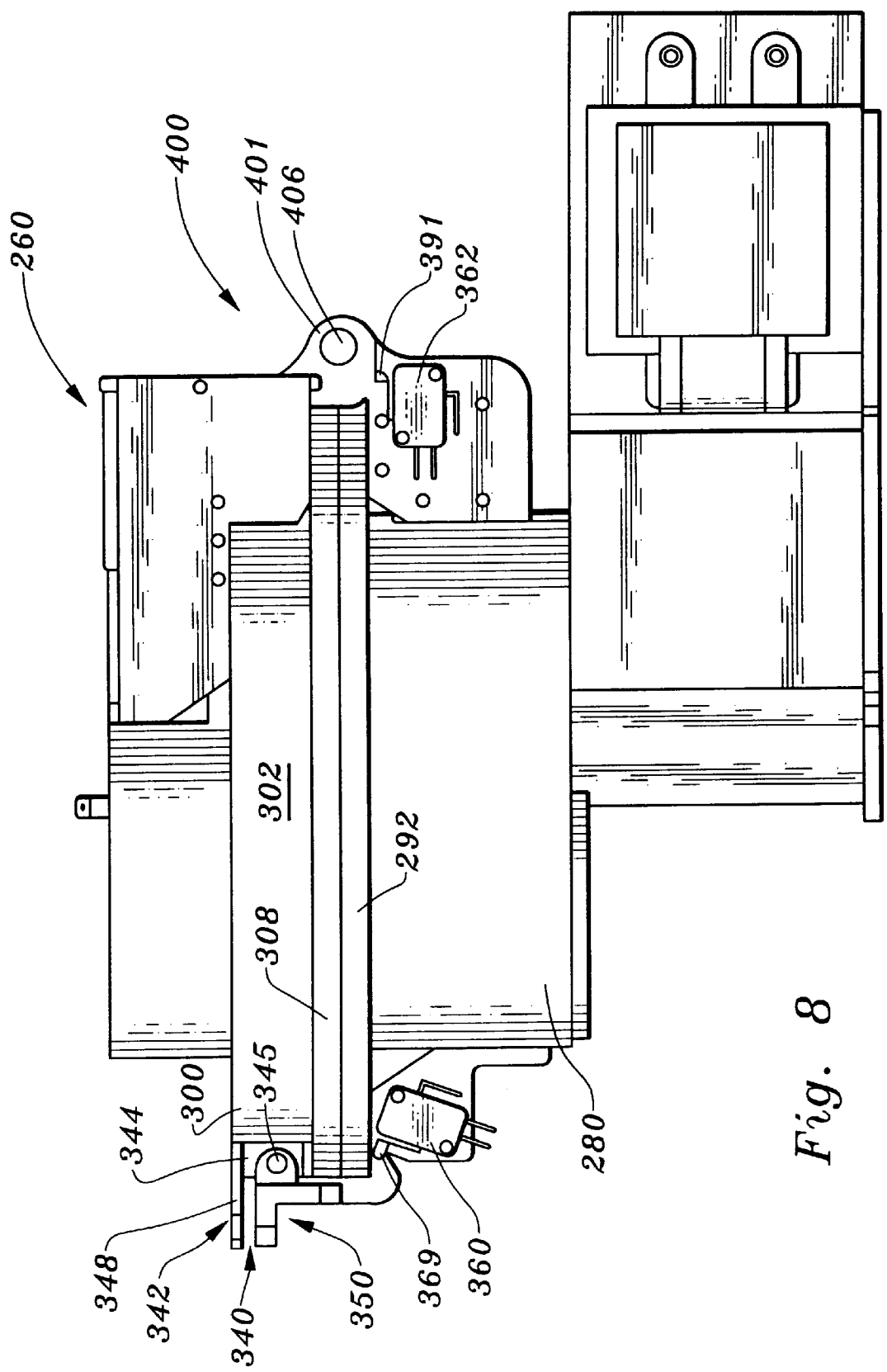
FIG. 8 is a right plan view of the microwave containment and analysis chamber, the wave guide, and a magnetron.
Figure 9:
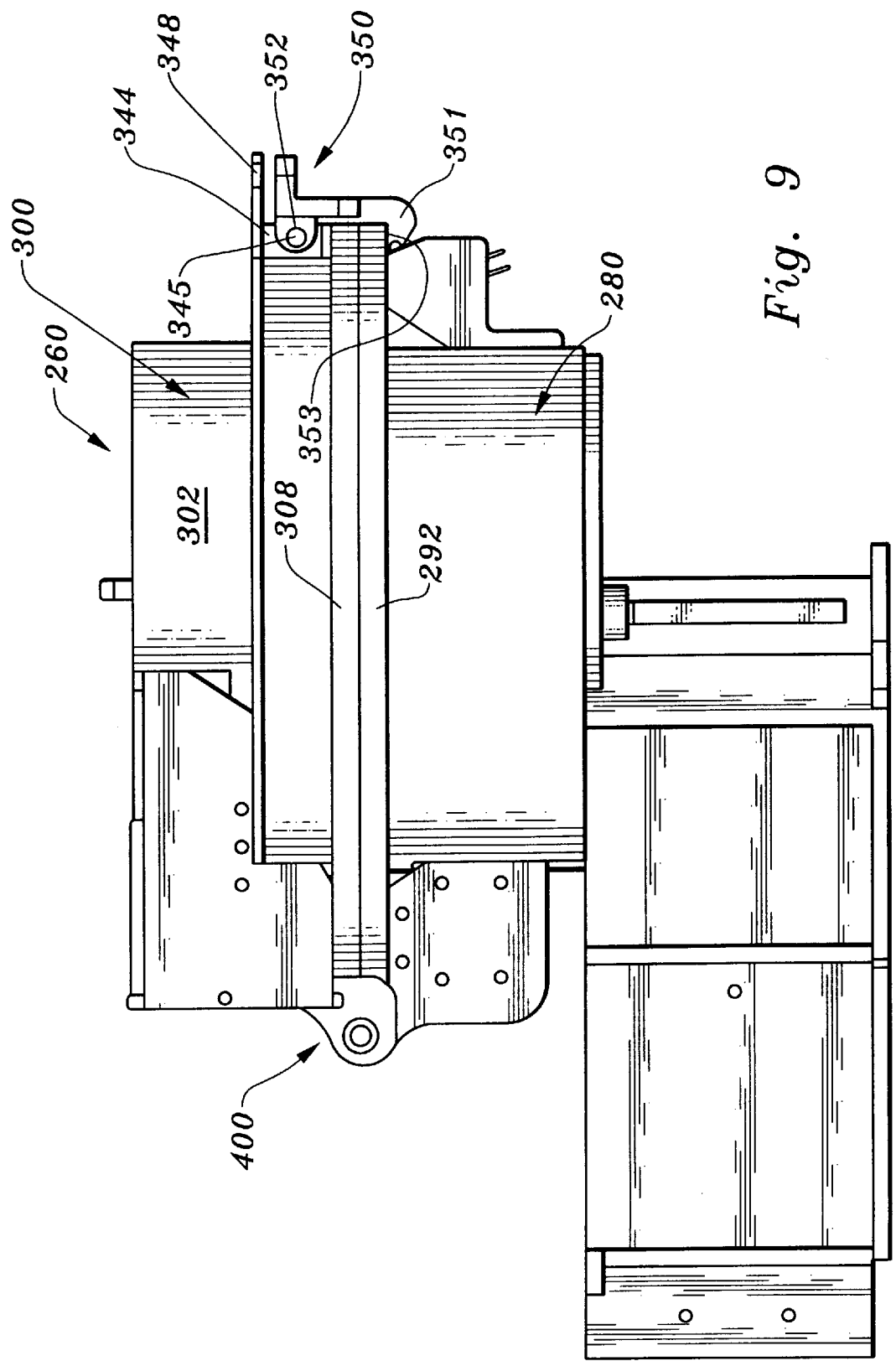
FIG. 9 is a left plan view of the microwave containment and analysis chamber and the magnetron.

Referring to FIGS. 8 and 9, a right plan view of the chamber 260 is shown with the latch means 340 securing the upper chamber 300 to the lower chamber 280. The latch is comprised of a stationary member 342 and a pivotable member 350. The stationary member 342 is substantially L shaped and includes a vertical member 344 extending up from the upper sealing flange 308 and transitioning into a horizontally extending member 348 which extends away from the cylindrical side wall 302 of the upper chamber 300. The stationary member 342 is provided with a pivot pin 345 in which the pivotable member 350 rotates thereabout for unlatching the upper chamber 300 from the lower chamber 280 thereby allowing the upper chamber to be moved from a substantially horizontal position to an upward vertical position. The pivotable member 350 is substantially J shaped and includes a pivot hole 352 operatively couple to the pivot pin 345. In a closed position, the J shaped member is rotated counter-clockwise such that an innerside of the tip 351 of the J shaped member is received on an underside 353 of the lower sealing flange 292 for locking the upper chamber to the lower chamber. Note that the outer side 369 of the tip 351 of the J shaped member 350 interacts with on/off lever of micro-switch 360 thereby closing the micro-switch and allowing power to be transferred to the power control module 122.

Figure 10:
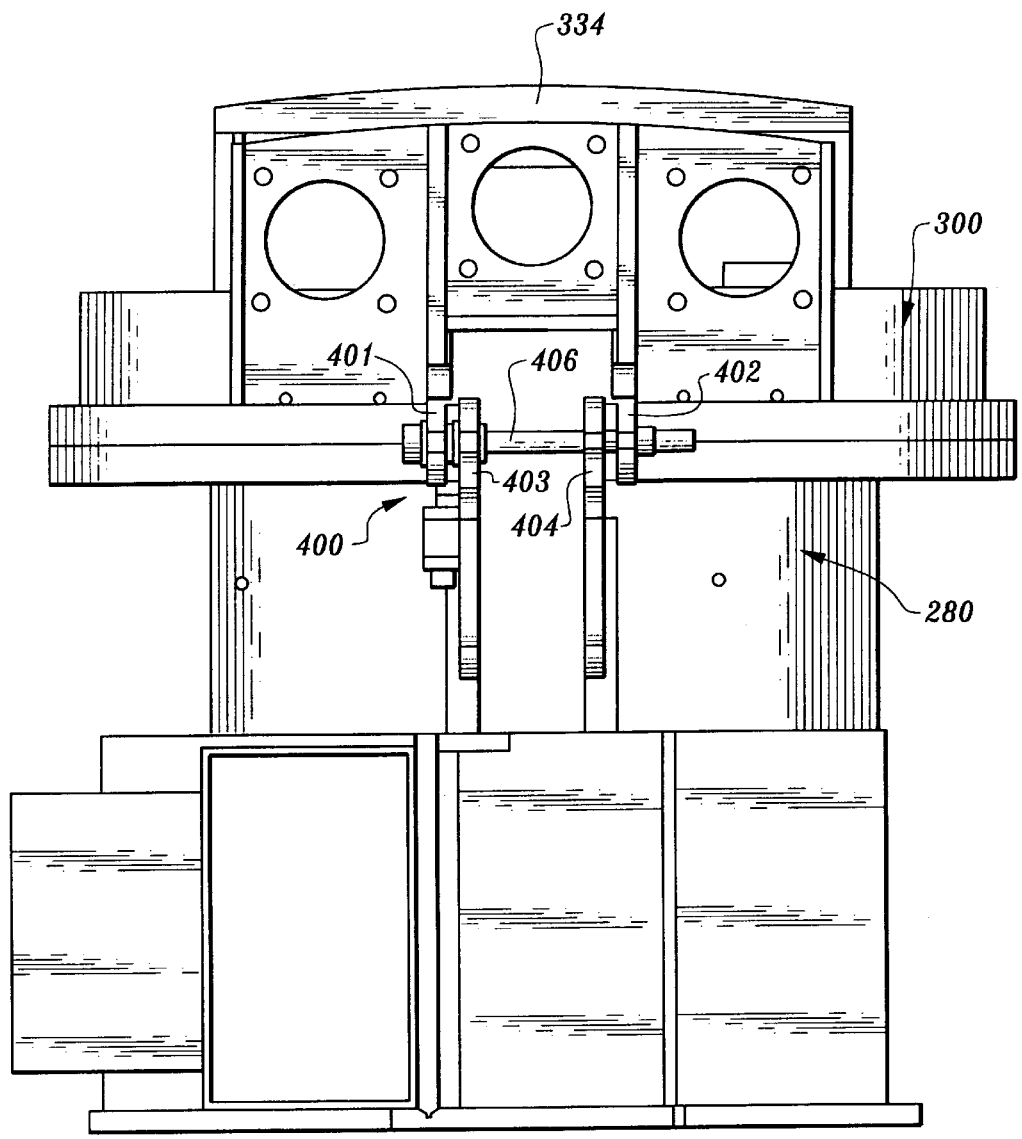
FIG. 10 is a back plan view of the microwave containment and analysis chamber, the magnetron and the wave guide.

Referring to FIGS. 8, 9 and 10, the upper chamber 300 is rigidly coupled to the lower chamber 280 via a pivotable hinge 400. The hinge 400 includes a pair of spaced apart upper flanges 401, 402 having holes disposed therein which are in axial alignment. A lower portion of the hinge 400 includes a pair of spaced apart lower flanges 403, 404 which reside within the spaced apart upper flanges 401, 402 of the upper portion of the hinge. The spaced apart flanges 403, 404 include holes which are axially aligned thereby allowing a pin 406 to extend through a first upper flange 401, a first lower flange 403, a second lower flange 404 and then a second upper flange 402 thereby allowing pivotable motion of the upper chamber 300 with respect to the lower chamber 280. The outer upper flanges of the hinge include outer lower surfaces which contact with an on/off lever 391 of at least the one micro-switch 362 for providing redundant protection from the magnetron being engaged prior to the sealing of the upper chamber with the lower chamber.

Figure 11:
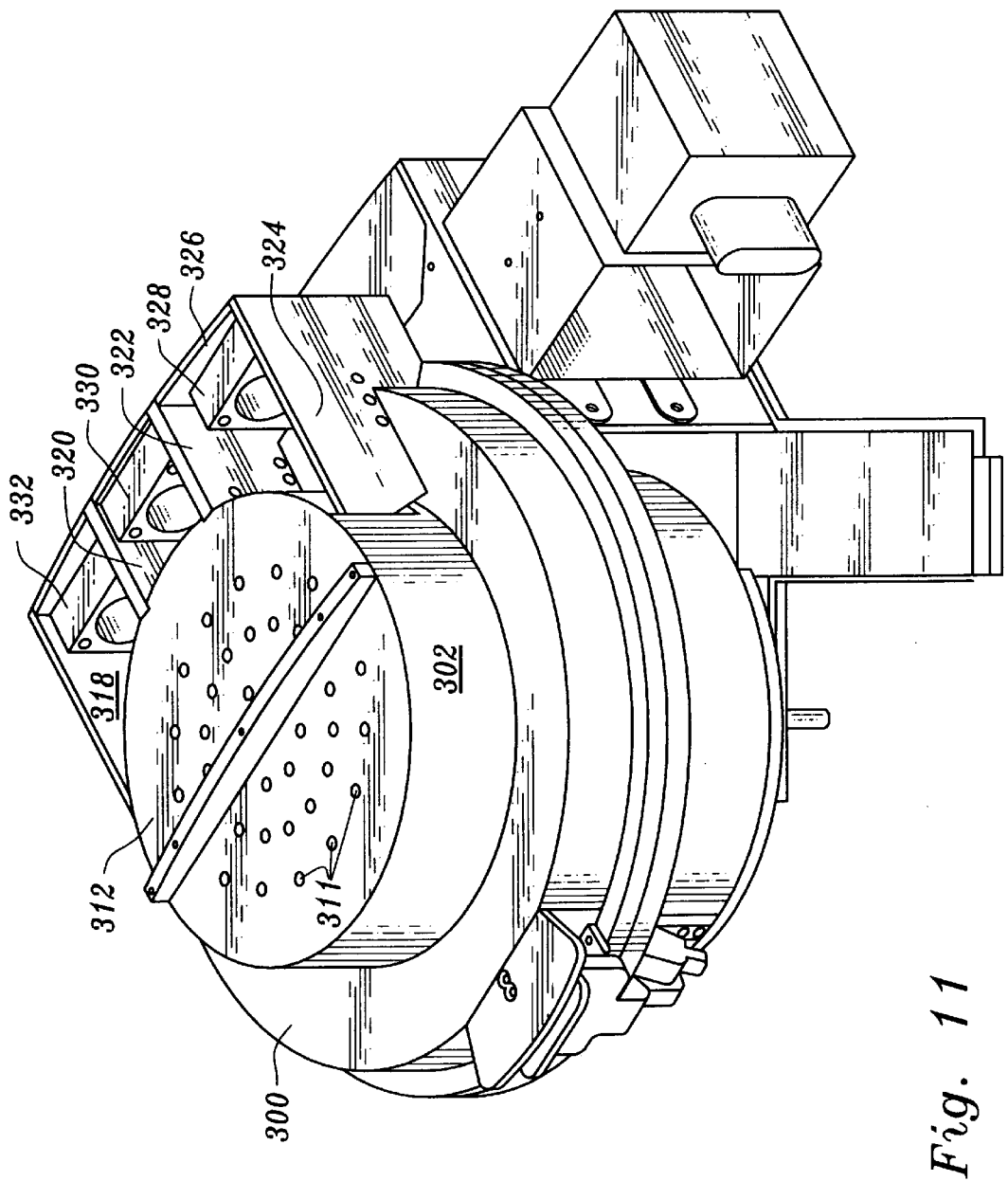
FIG. 11 is a front side elevational view of the microwave containment and analysis chamber, with a top cover removed therefrom.

Referring to FIGS. 10 and 11, the upper chamber 300 includes a moisture evacuation chamber disposed on top of the upper cylindrical wall 302 defining the microwave containment cavity of the upper chamber. The top plate 312 of the upper chamber has perforations 311 which allow moisture to pass therethrough without the exhausting of microwaves. The moisture is aspirated by a plurality of fans 328, 330 and 332 disposed on a back wall 326 of each of the three evacuation channels defined by a pair of outer channel walls 318, 324 and a pair of inner channel walls 320, 322 as shown in FIG. 11. Preferably, the fans are on during intense (high power) moisture volatilization and then shut off for end point determination. A dome shaped lid 334 (FIG. 7) covers the perforated top plate 312 of the upper chamber 300 and the evacuation channels wherein the fans are disposed. The fans 328, 330 and 332 can be operatively coupled to the power control module or to the central processing unit for delivering power to the fans either in a direct or controlled manner.

Figure 12:
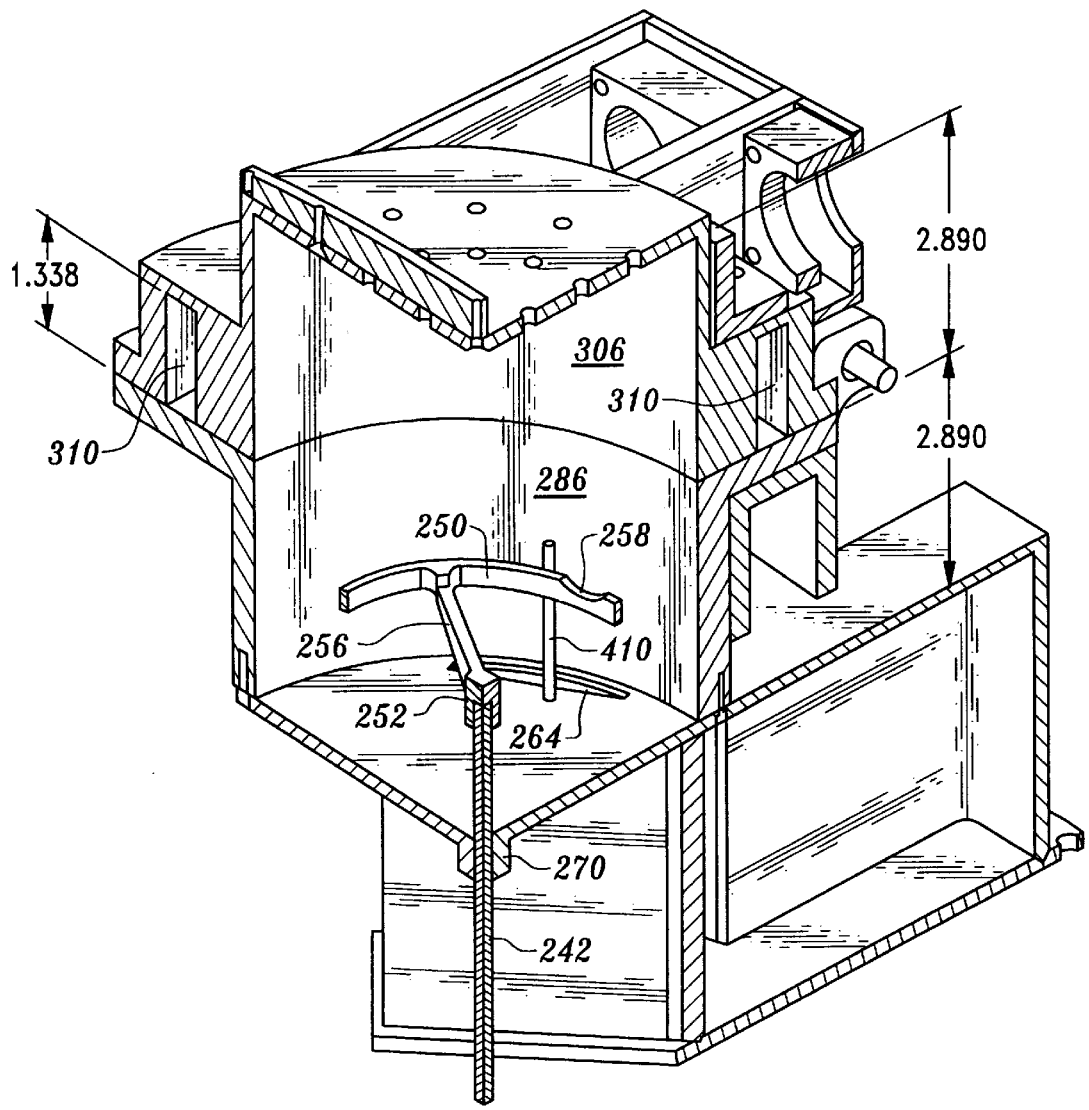
FIG. 12 is a cut-away view of the microwave containment and analysis chamber according to the instant invention.

Referring to FIG. 12, a cut-away view of the microwave containment chamber in a closed position is shown thereby revealing a microwave choke channel 310 disposed in the upper sealing flange 308 of the upper chamber and having a height of 1.338 inches. The choke geometry traps and reflects U wave energy at ¼ wavelength to cancel the effectiveness of the energy. The choke channel 310 is a re-active choke system which presents a short-circuit impedance between the sealing flanges of the chamber 260 even if they are slightly separated or misaligned. In addition, the cut-away view reveals a first tuning rod 410 and portal 264 wherein the tuning rod 410 extends from the base plate 262 across the portal opening and into the cylindrical side wall 286 defining the lower chamber of the microwave containment chamber. In addition, a cut-away view of a carriage 250 for supporting a sample is shown wherein the carriage 250 is operatively coupled to the weighing rod 242 extending through the centralized bore 270 of the base 262 of the lower microwave containment chamber 280.

Figure 13:
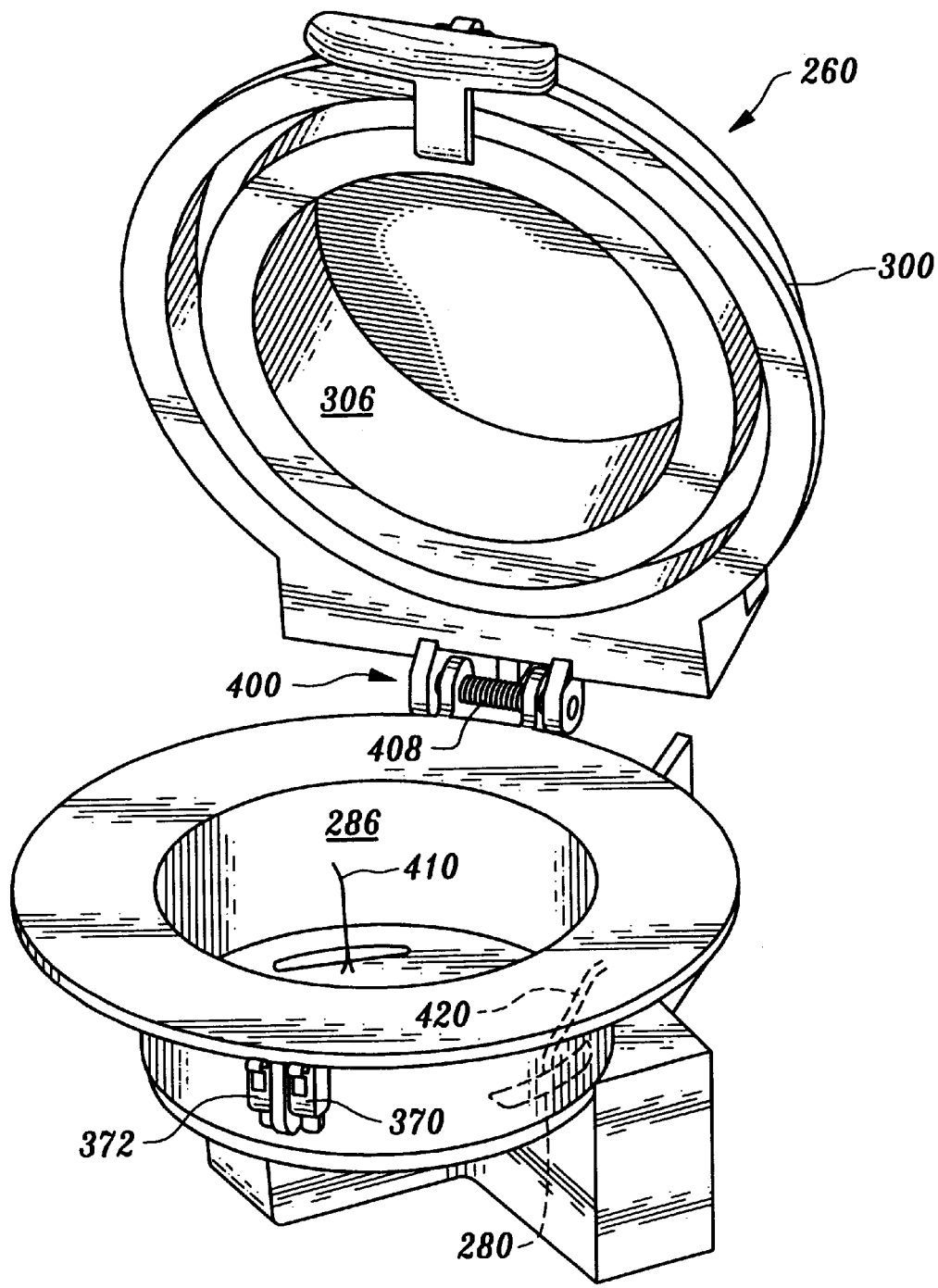
FIG. 13 is a front side elevational view of the microwave containment and analysis chamber in an open position and revealing a pair of tuning rods.

Referring to FIG. 13, the microwave containment and analysis chamber 260 is shown in an opened position thus revealing the spring biasing means 408 coupled to the hinge 400 rigidly attaching the upper microwave chamber 300 with the lower microwave chamber 280 and providing means for retaining the upper microwave chamber in an opened position for ease of loading a sample onto the carriage 250. The interior cylindrical wall 306 of the upper chamber has a height of 2.890 inches and an interior diameter of 6.340 inches. The annulus choke channel 310 circumscribing the cylindrical wall of the interior of the upper chamber is spaced therefrom and has an inner diameter of 8.023 inches and an outer diameter of 8.887 inches thereby defining a choke channel having a circular width of 0.864 inches and a height of 1.338 inches. The interior cylindrical wall 286 of the bottom chamber 280 has a diameter of 6.340 inches which is the same diameter of the interior cylindrical wall 306 of the upper chamber 300. The height of the interior cylindrical wall 286 of the lower chamber 280 is 2.890 inches which is also equal to the height of the interior wall 306 of the upper chamber 300. FIG. 13 also reveals a pair of tuning rods disposed substantially in quadrature, specifically, separated by 93.4 degrees. The tuning rods 410, 420 will be delineated in detail with respect to FIG. 17. Furthermore, note that two micro-switches 360, 362 are provided to interact with the latch 340 for securing the upper chamber 300 to the lower chamber 280.

Figure 14:
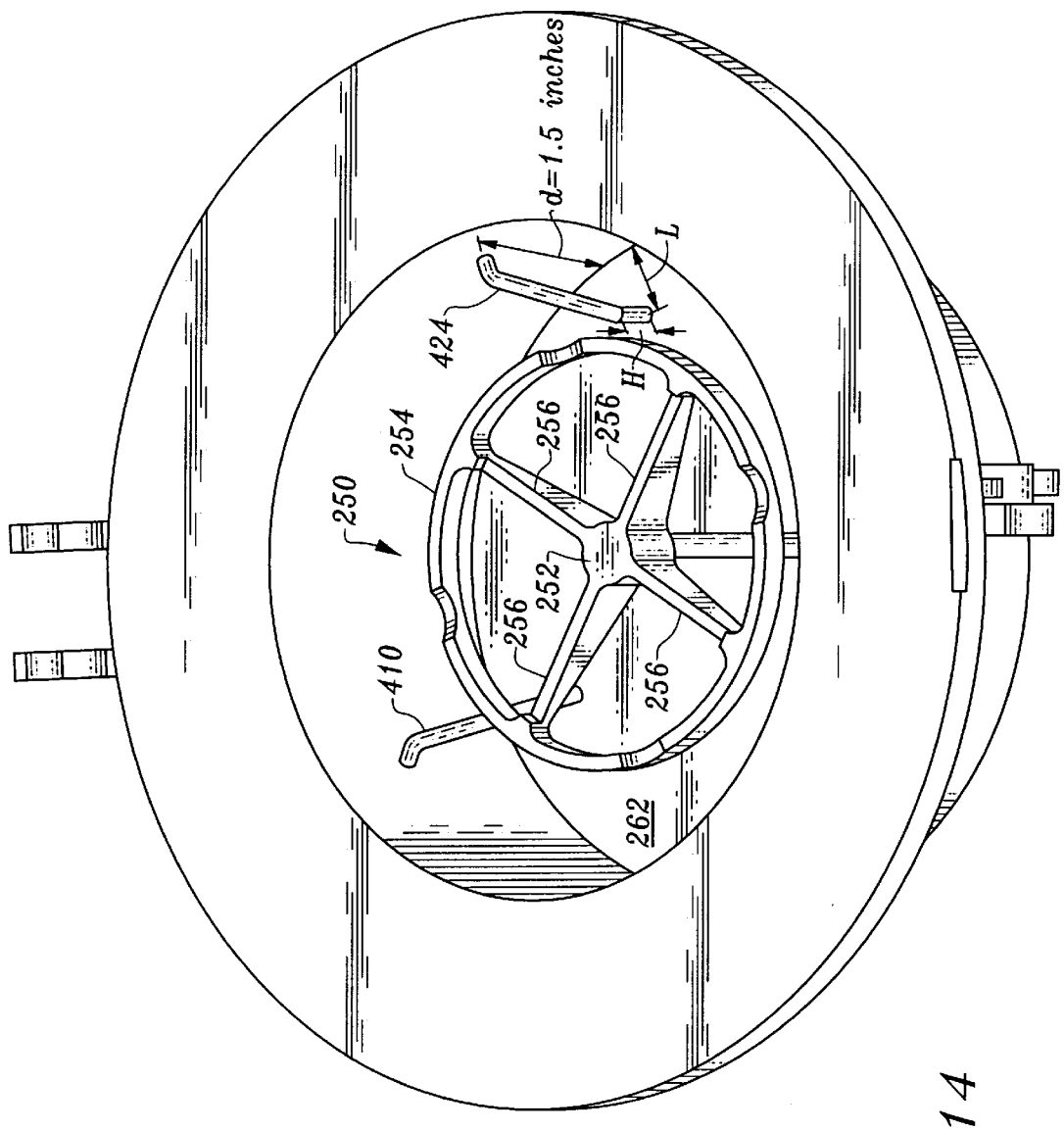
FIG. 14 is a top elevational view of the lower microwave chamber showing the carriage operatively coupled to a wave rod and tuning rods disposed within a lower base plate and a cylindrical side wall.
Figure 15:
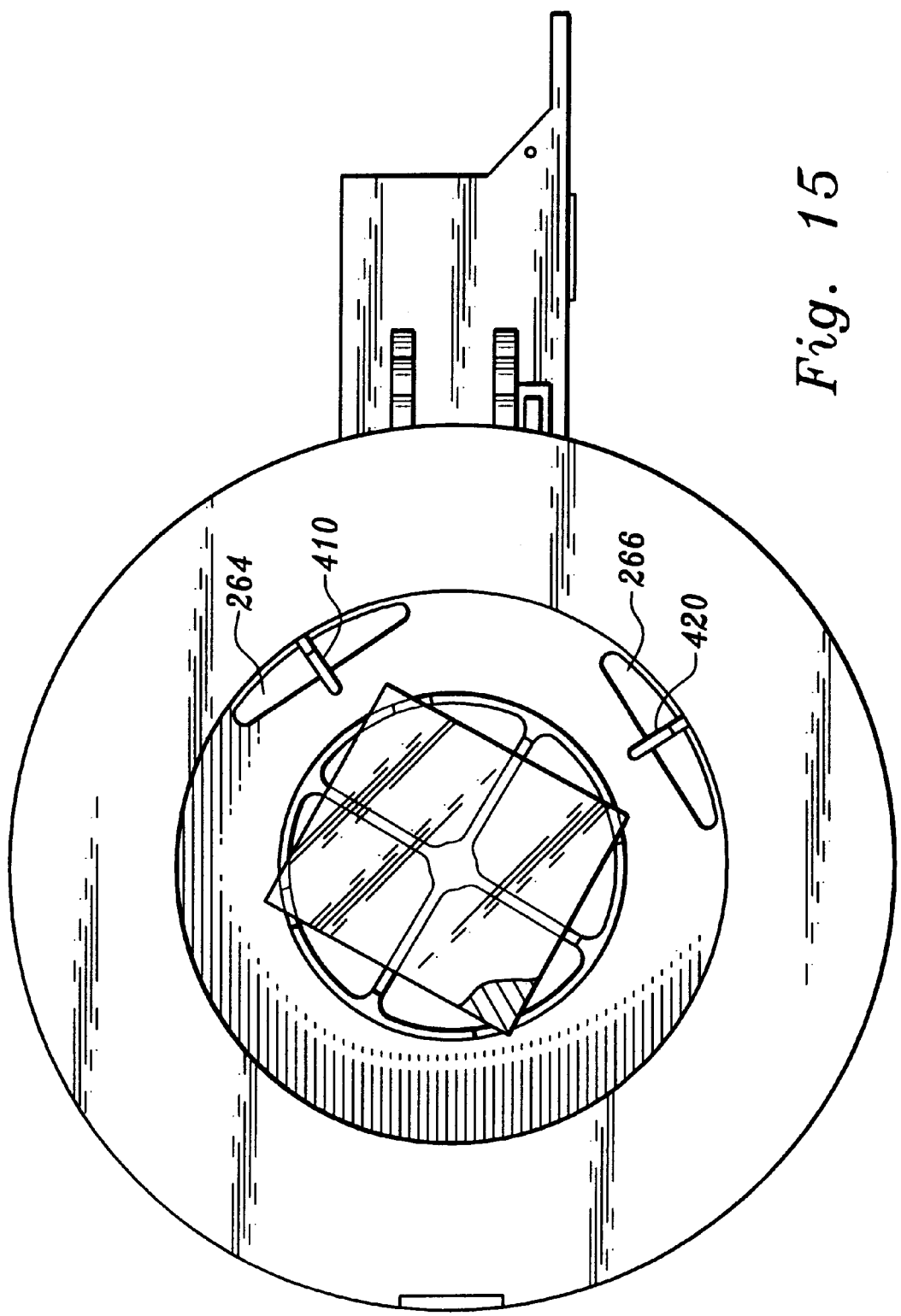
FIG. 15 is a top plan view of the lower microwave chamber showing the tuning rods traversing a pair of portals.

Referring to FIGS. 14 and 15, the carriage 250 is configured as a spoked shaped wheel having a central hub 252, a plurality of spokes 256 and an outer rim 254 wherein the central hub transitions into preferably four equally spaced apart spokes 256 terminating into the substantially circular outer rim 254. The outer rim 254 is provided with a plurality of notches 258 off set from the spokes and preferably equally spaced one from another. The hub 252 of the carriage includes a blind bore which couples to the weighing rod 242 extending through the base 262 of the lower chamber 280. In addition, the tuning rods 410, 420 are shown to be disposed in the base 262 of the lower chamber 280 at a distance distal from the interior cylindrical wall 286. The tuning rods 410, 420 each include a first end and a second end. The first end 412, 422 (FIG. 16b) of the tuning rods is disposed in the base 262 of the lower chamber 280 and then transitions into medial portions 414, 424 which are angled toward the interior side wall 286 of the lower chamber wherein the tuning rods terminate into a substantially horizontal end 416, 426 which is received in apertures disposed in the cylindrical side wall of the lower chamber. Note that each tuning rod has a height H in which it vertically extends from the base before transitioning into its medial portion which angles toward the cylindrical lower interior wall of the lower chamber. The tuning rods are tolerenced around a nominal diameter. In addition, the tuning rods are spaced a distance L away from the cylindrical interior wall such that the rods 410, 420 straddle the portals 264, 266 respectively. See also FIG. 23.

The tuning rods preferably bisect the portals at a median location wherein the portals are divided into equally spaced sectors. The tuning rods 410, 420 have a diameter of 0.094 inches. As shown in FIGS. 16a, 16b, the tuning rods include medial portions 414, 424 with first ends 412, 422 and second ends 416, 426. Each first end having a length of 0.200 inches and the second end of a length of 0.500 inches. The height between the first end and a bend interposed between the medial portion and the second end is equal to 0.62 inches. The length between the second end and the bend interposed between the first end and the medial portion is equal to 1.488 inches. Thus, an angle between the base plate and the tuning rod can be defined as approximately the inverse tangent (arctangent) of the length of the side opposite the angle divided by the height between the first bend and the second bend as shown in the drawings. Please also see FIG. 23.

TUNING ROD DESCRIPTION

The apparatus 10 has a cylindrical microwave applicator including two control rods or tuning rods 410, 420. Most microwave applicators (cavities) are of the type "multi-mode", which refers to the amount of different mode patterns that can exist in the cavity for a given frequency. In our application we have two basic modes, one being $TM_{012}$ and the other being $TM_{111}$. To be able to optimize the heat-distribution it is essential to be able to control the mode balance between the two modes. This is normally practiced by designing the microwave inlet coupling (particularly the position) in such a way that desired balance is maintained for some predefined conditions. In this case with the specific modes it is not possible to achieve suitable balance with traditional means.

The instant invention includes the use of coupling-hole(s) (irises) or portals between the waveguide(s) and cavity. The basic idea with the tuning rod is to disturb the electric field of mode that is to be suppressed (in this case $TM_{012}$). This mode has its electric field going in an arc of the total height of the cavity (rotational symmetrical), side wall of the cylinder. By introducing a metal rod semi parallel to the electrical field, one will disturb the mode and with that suppress its existence. The more parallel and the closer to its maximum of the effective to place the control rod in the near field of the inlet-coupling hole or portal is superior to arbitrary placement in the cavity. The preferred placement is just in front of the coupling hole on the cavity side of the coupling hole.

Referring to FIGS. 13 through 17 the tuning rods 410, 420 are between the cylindrical side wall above the coupling slots or portals and the flat circular wall or base some distance inwards radially. The general geometry is shown in FIGS. 14, 16a and 16b. There are two perpendicular slots or portals fed in (almost) quadrature. The system in FIG. 1 is doubled.

It has been found that the tuning rods provide a positive action, resulting in a stabilization of the impedance matching of the apparatus 10 (this is crucial, since the load is small).

THE CAVITY FEED AND POSSIBLE MODES

The apparatus is supposed to have two resonances: $TM_{111}$ and $TM_{012}$.

RESONANT ACTION OF THE DEVICE STRUCTURE

One may invision the tuning rod situation by supposing that two oppositely propagating waves from one narrow wall to the other interface in such a way that maximum field strength is obtained with minimum energy input—which is a very suitable way of defining resonance here.

Figure 23:
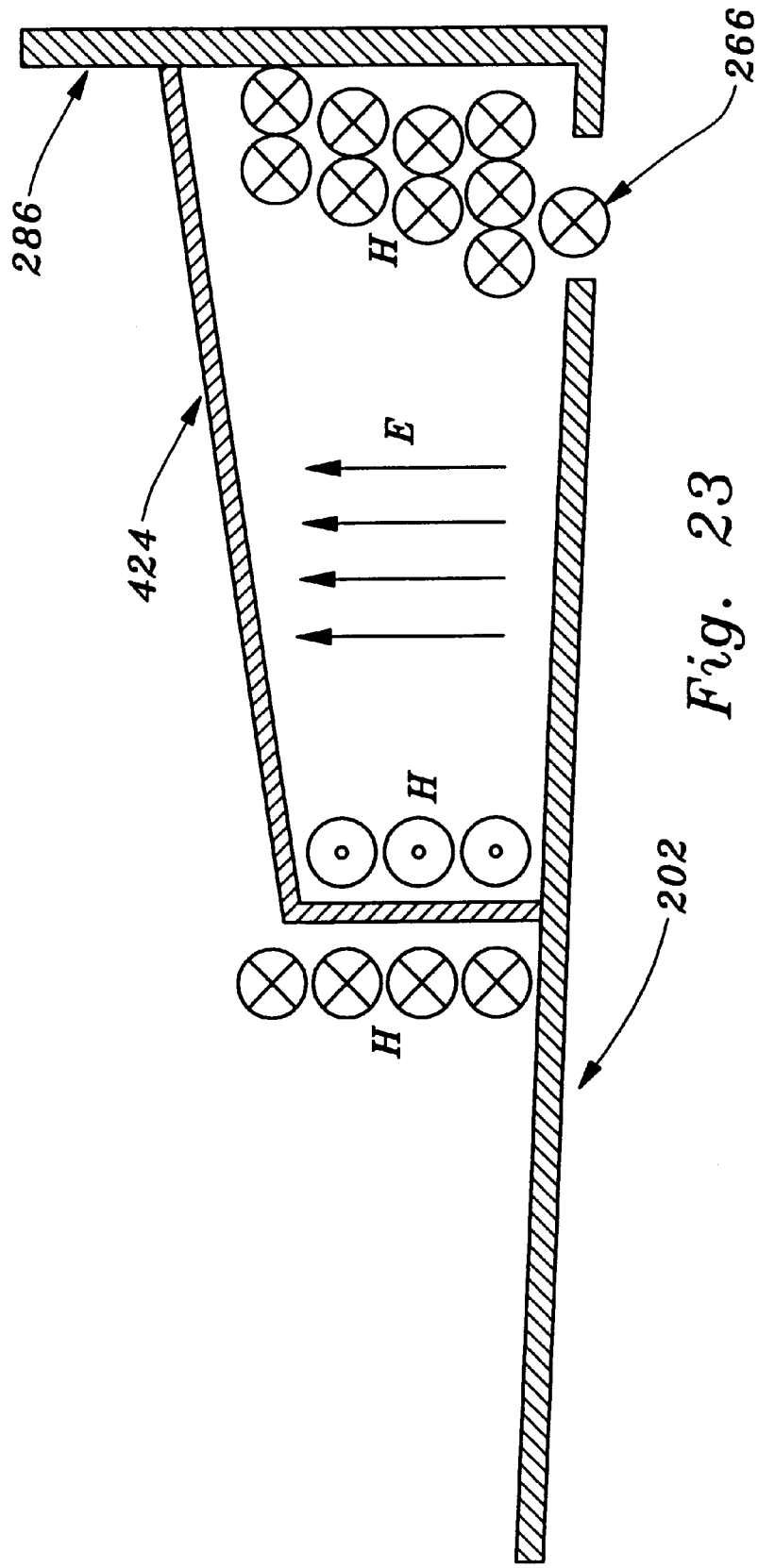
FIG. 23 is a side view of a tuning rod disposed over a portal.

What does the resonance result in?—The simplest answer is that a maximum part of the available power flow is "converted" to the resonant field pattern; when this happens there will be less impinging power left so that the resonance will be self-limiting in amplitude. Generally, there will be an almost full nulling of one impinging field component by the resonant field. This situation is shown in FIG. 23.

In effect, the incoming H field from each slot or portal will create a resonance (if the device dimensions are right) which will weaken the total H field at the wall in the region. Instead, there will be a strong H field around (and particularly outside) the "inner leg" 412, 422 of the device, where there is no strong field without the device.

It is readily seen that the inner leg will act as a quite powerful exitator of a circulating H field, which will go over into a vertical E field upwards. This combination of E and H fields may couple quite well to a H field loop (with accompanying vertical E field) of the $TMz_{11}$ mode. There will thus be a good field matching from the device region (medial portion 414, 424) to the desired cavity mode.

THE COUPLING BETWEEN THE CAVITY AND DEVICE REGION RESONANCES

This coupling function can be explained as follows: the coupling factor (in principle: transmission impedance equality) between the resonant device region and the cavity resonance will become quite frequency-sensitive, due to the reasonably high Q value of the device region. If the device region is now chosen to be resonant at a frequency some ten(s) of MHz away from 2460 MHz, the cavity resonance with a changing (i.e drying) load will move along the resonant curve of the device region.

If the Q value of the cavity is high, its own resonance will dominate and the coupling is good. When the cavity Q value goes down, the coupling will typically be less (since high coupling for a small sample is desirable). However, the overall resonant frequency will change less due to the resonance coupling between the two resonances. Furthermore, the coupling can be made to increase (due to the slope of the device region being active at the "start" of the process), and the impedance matching can be made fairly constant during the whole process.

There are thus several parameters which together determine if the combination of cavity and device region will work well:

The resonant frequency of the cavity resonance without device (and at strong undercoupling), as a function of the load variations.

The Q value of the cavity resonance, and its variation with the specified load variations.

The field matching of a primary (slot) feed to the resonant mode(s) (this contributes to the determination of also the coupling factor).

The field matching of the device region to the cavity mode (this contributes to the determination of also the coupling factor).

The resonant frequency of the device region (under conditions of removed cavity).

The internal Q value of the device region.

The coupling factor from the slot to the cavity resonance, as a function of the load variations.

The coupling factor from the slot to the device region (i.e. how much of the overall coupling is determined by the device region).

Figure 17:
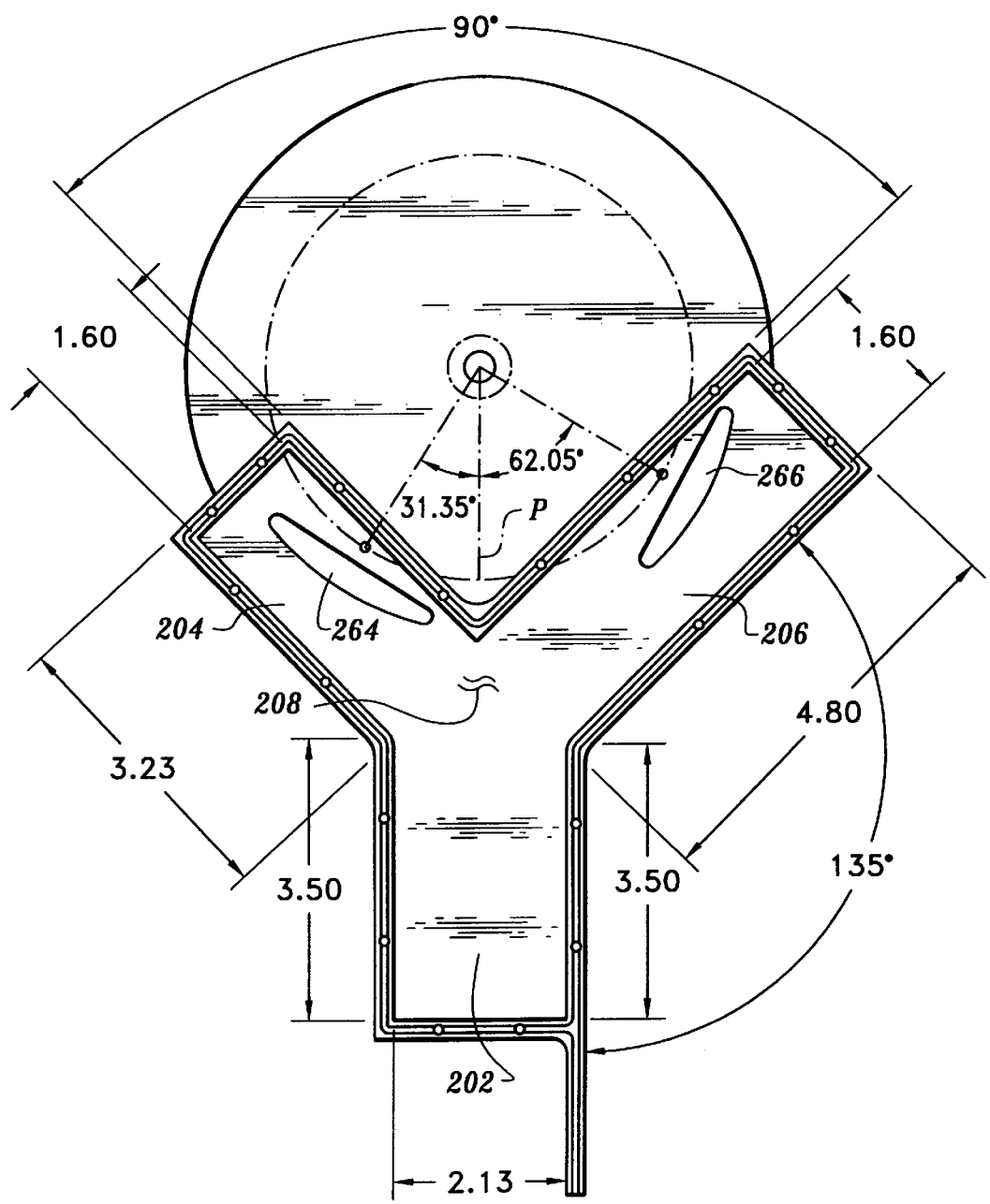
FIG. 17 is a bottom plan view of the microwave containment and analysis chamber and the wave guide with important dimensions delineated thereon.
Figure 18:
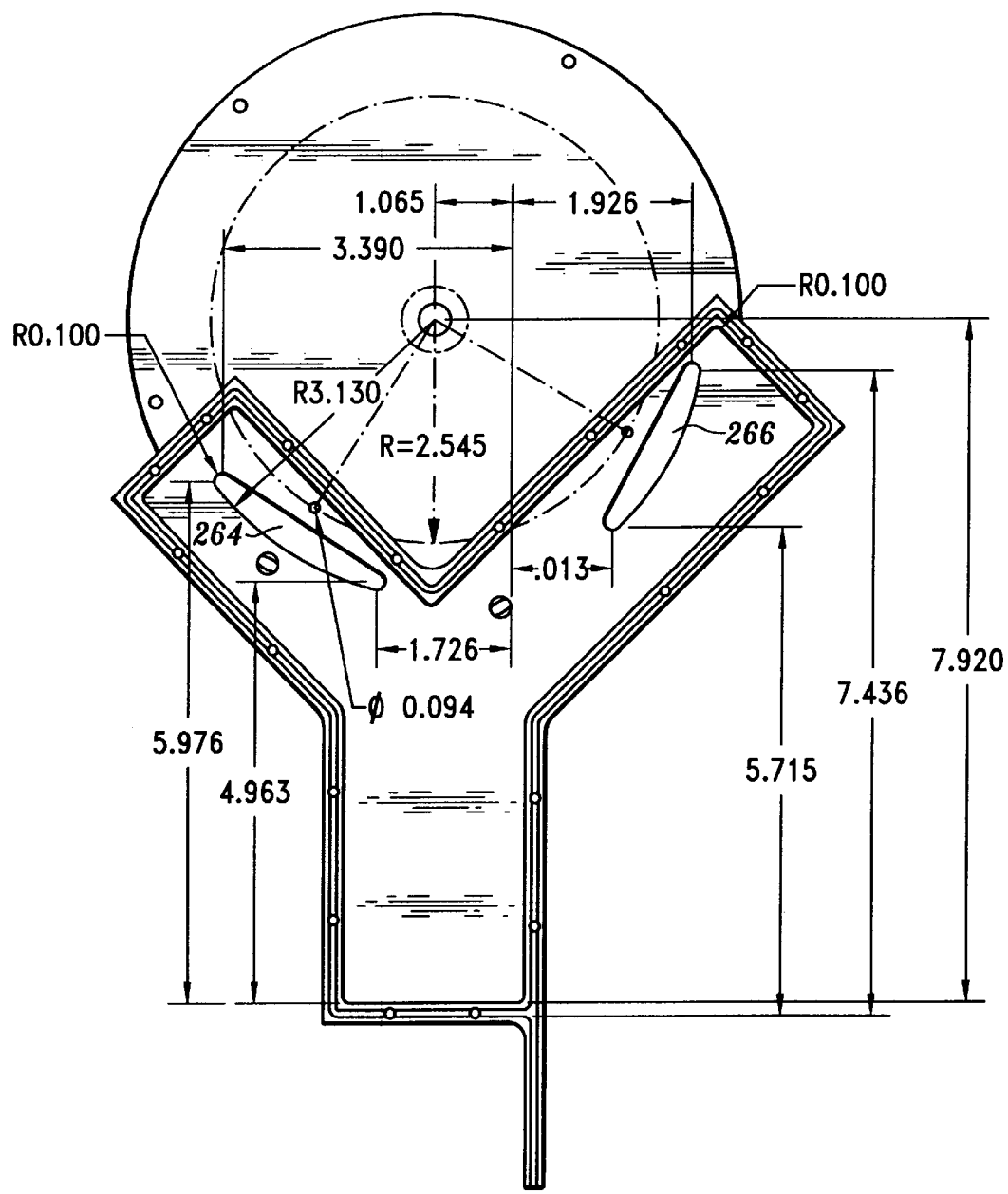
FIG. 18 is a bottom plan view of that which is shown in FIG. 9 with further dimension depicted thereon.

The unique configuration and dimensions of the wave guide will be delineated with the help of FIGS. 17 and 18. The wave guide is substantially Y shaped having a base wave guide 202 which is approximately 3.5 inches in length and 2.13 inches in width, the first wave guide feed 204 having a length of 3.23 inches and a width of 1.6 inches, and the second wave guide feed 206 having a length of 4.8 inches and a width of 1.6 inches. The first and second wave guide feeds 204, 206 bifurcate from the main wave guide at a intermediate junction 208. A splitter can be added at the junction to assist in setting up the phase shift. The first wave guide feed 204 transitions into the first portal 264 disposed in the base 262 of the lower chamber 280 while the second wave guide feed 206 transitions into the second portal 266 disposed in the base plate 262 of the lower chamber 280. The mid-point of the first portal is at a 31.35 degree angle with respect to a plane P bisecting the transitional area of the first wave guide feed and the second wave guide feed. The mid-point of the second portal has an angle of 62.05 degrees with respect to this bisecting plane as is shown in FIG. 17.

Referring to FIG. 18, the portals 264, 266 of the base 262 provide openings for delivery of microwave energy to the sample being assayed and subsequently manipulated for a loss on drying analysis. The portals 264, 266 are substantially canoe shaped openings having radiused bottoms of preferably 3.130 inches away from a mid-point of the centralized bore disposed in the base of the lower chamber. The radiused bottom transitions into radiused corners having a 0.1 inch radius and a cord extending from one radiused edge to the other thereby forming a closed canoe shaped opening.

Figure 19:
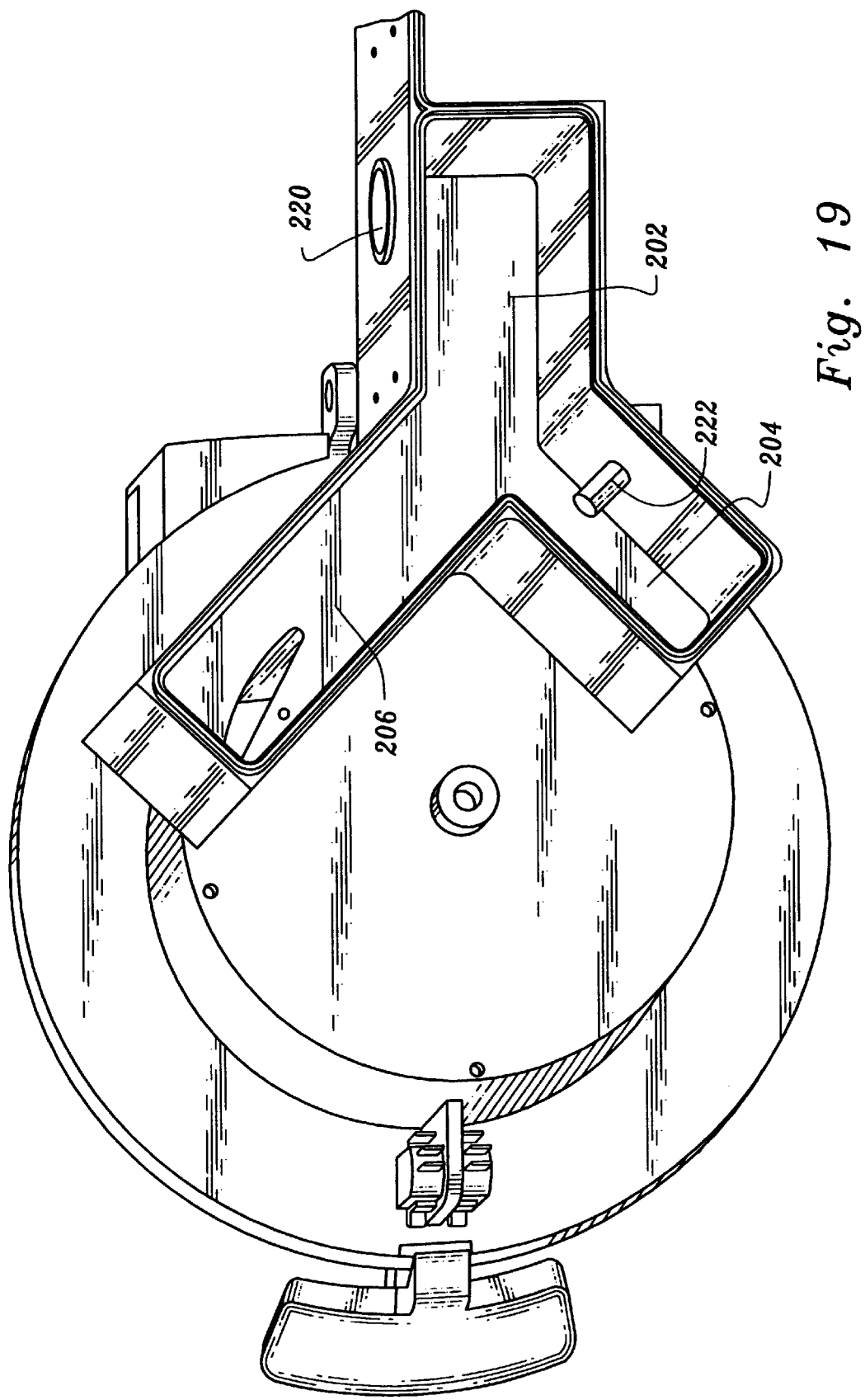
FIG. 19 is a bottom view of the wave guide with a base of the wave guide removed therefrom for showing a tuning stub disposed through an outer peripheral wall of one branch of the wave guide.
Figure 20A:
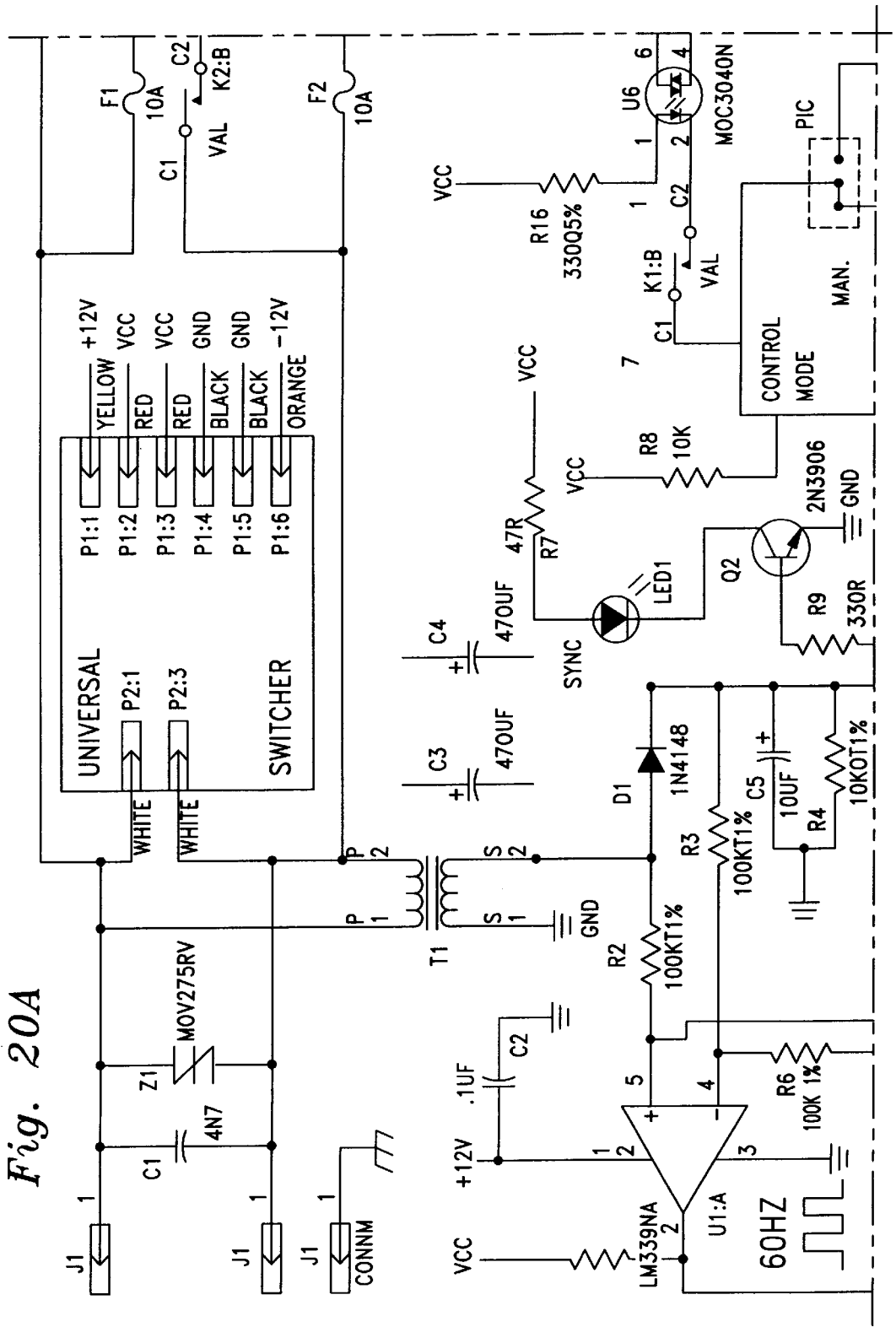
FIG. 20 is a schematic of the power control module shown in FIG. 6.
Figure 20B:
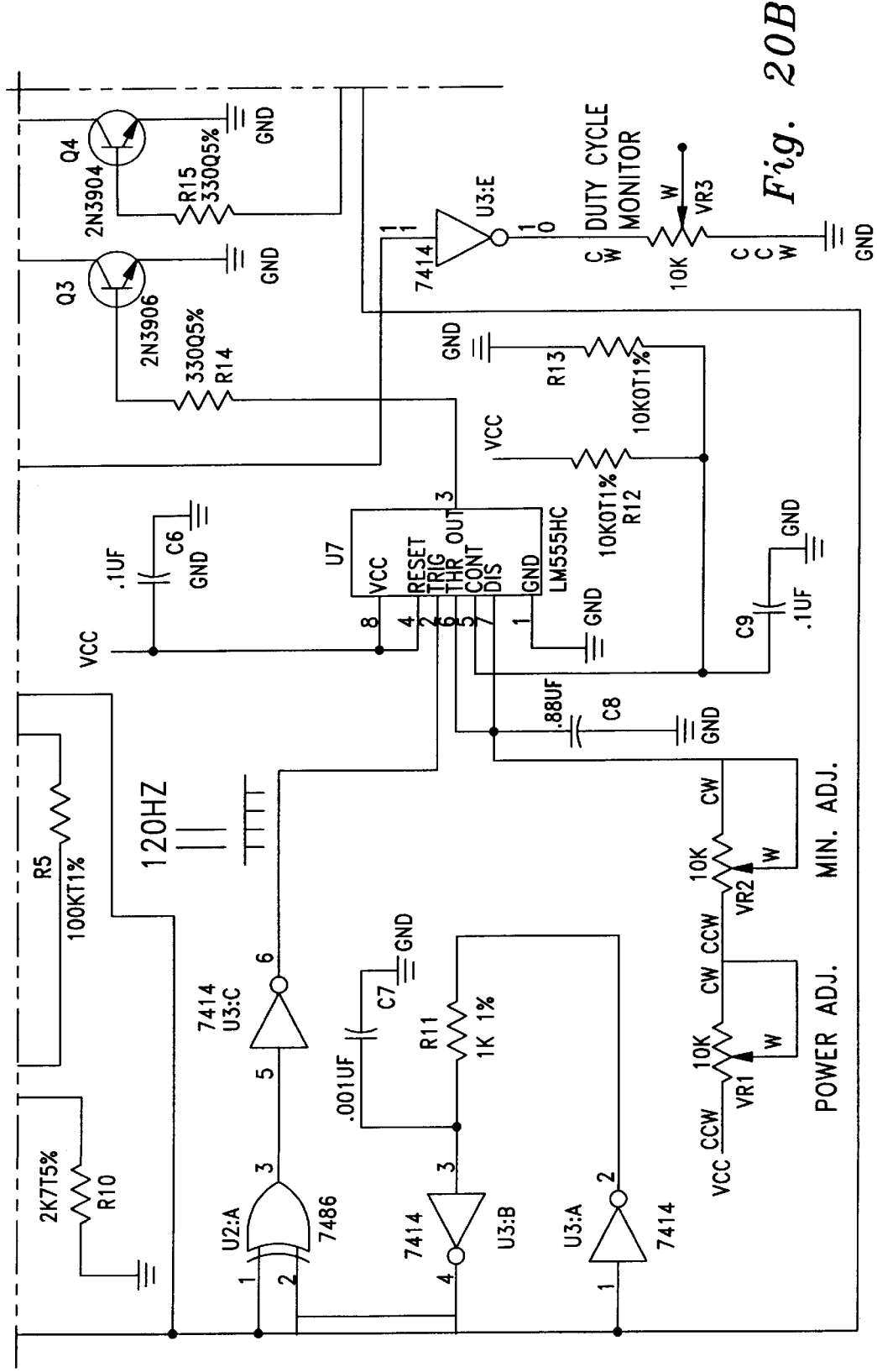
Figure 20C:
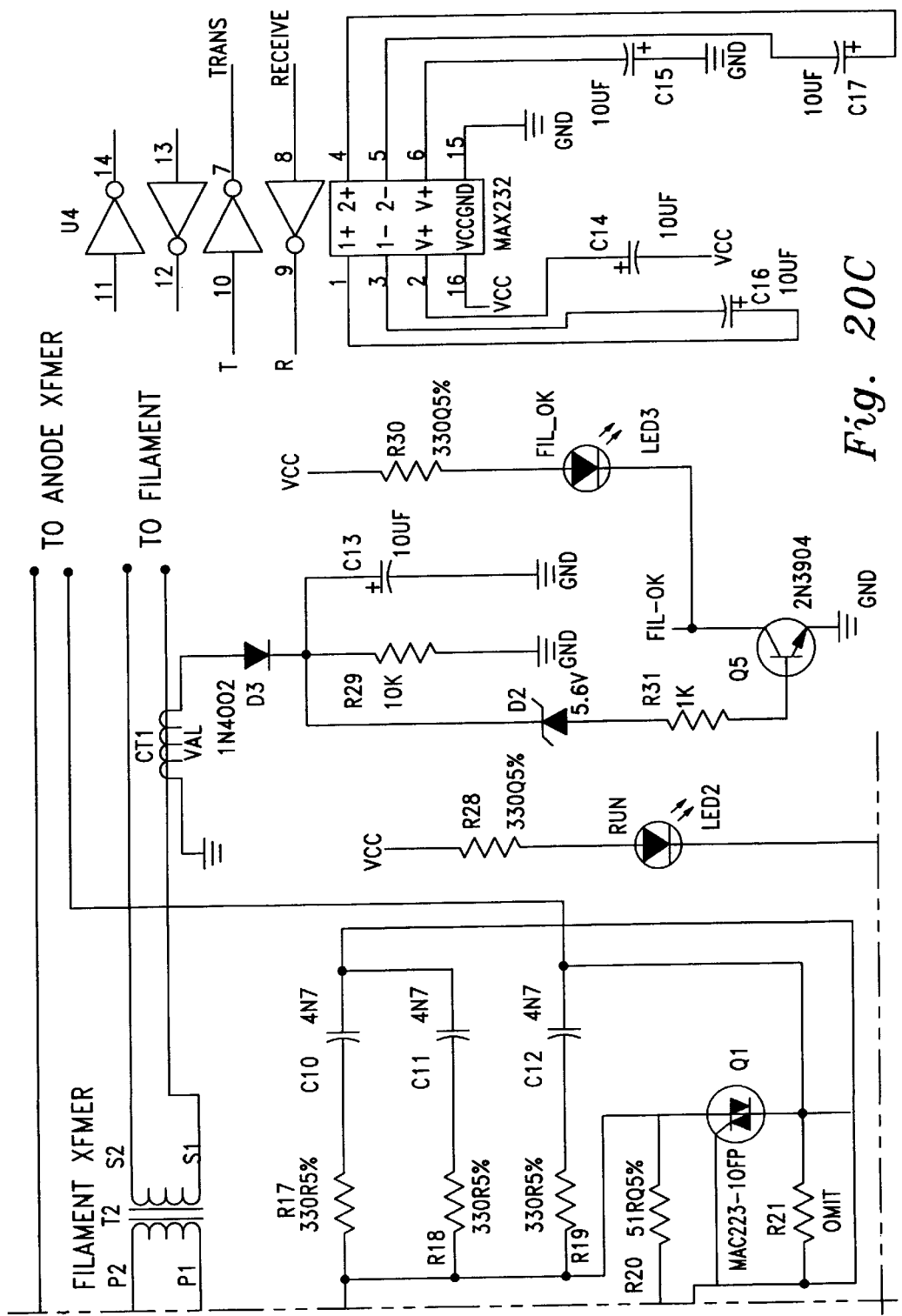
Figure 20D:
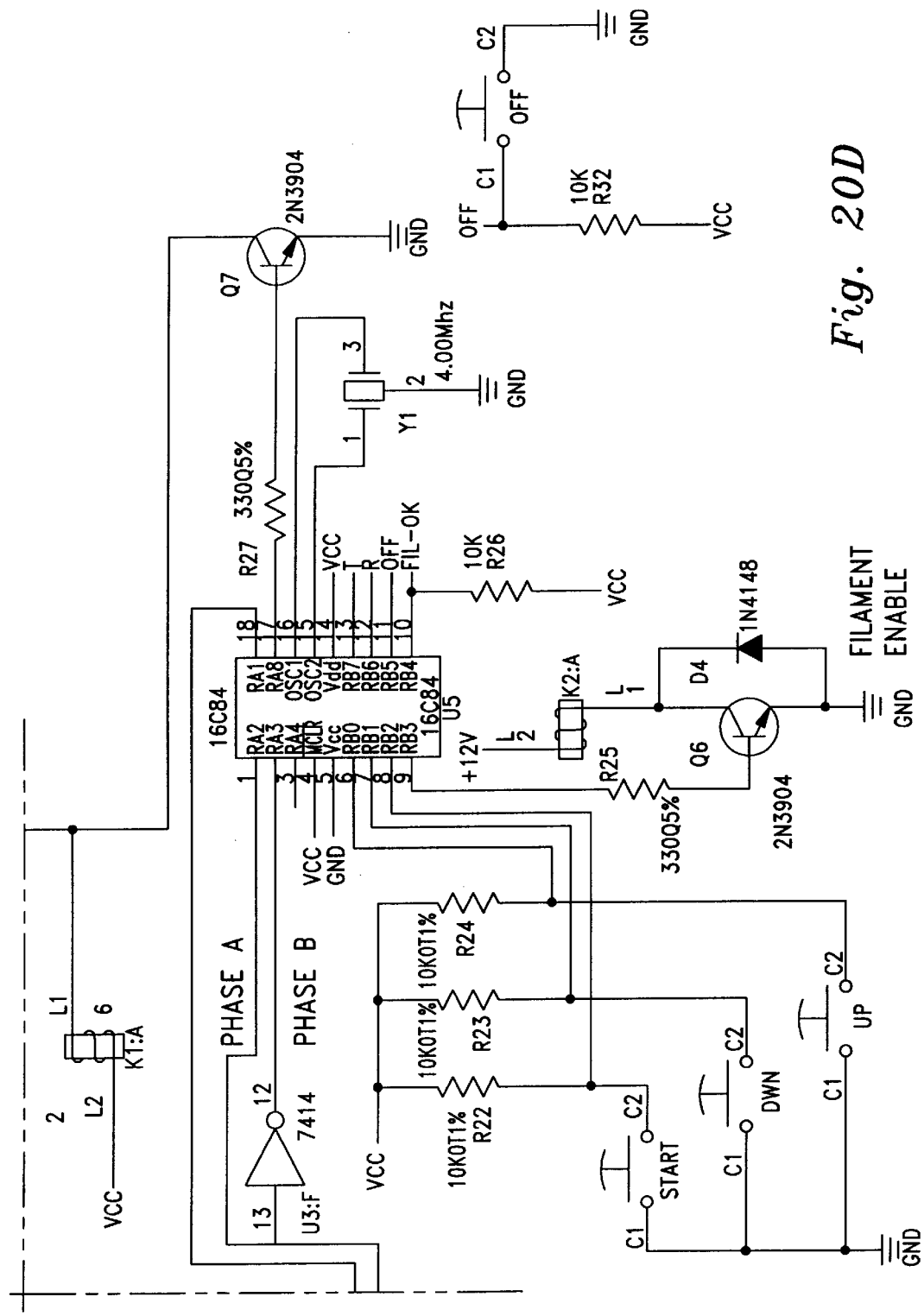
Figure 21A:
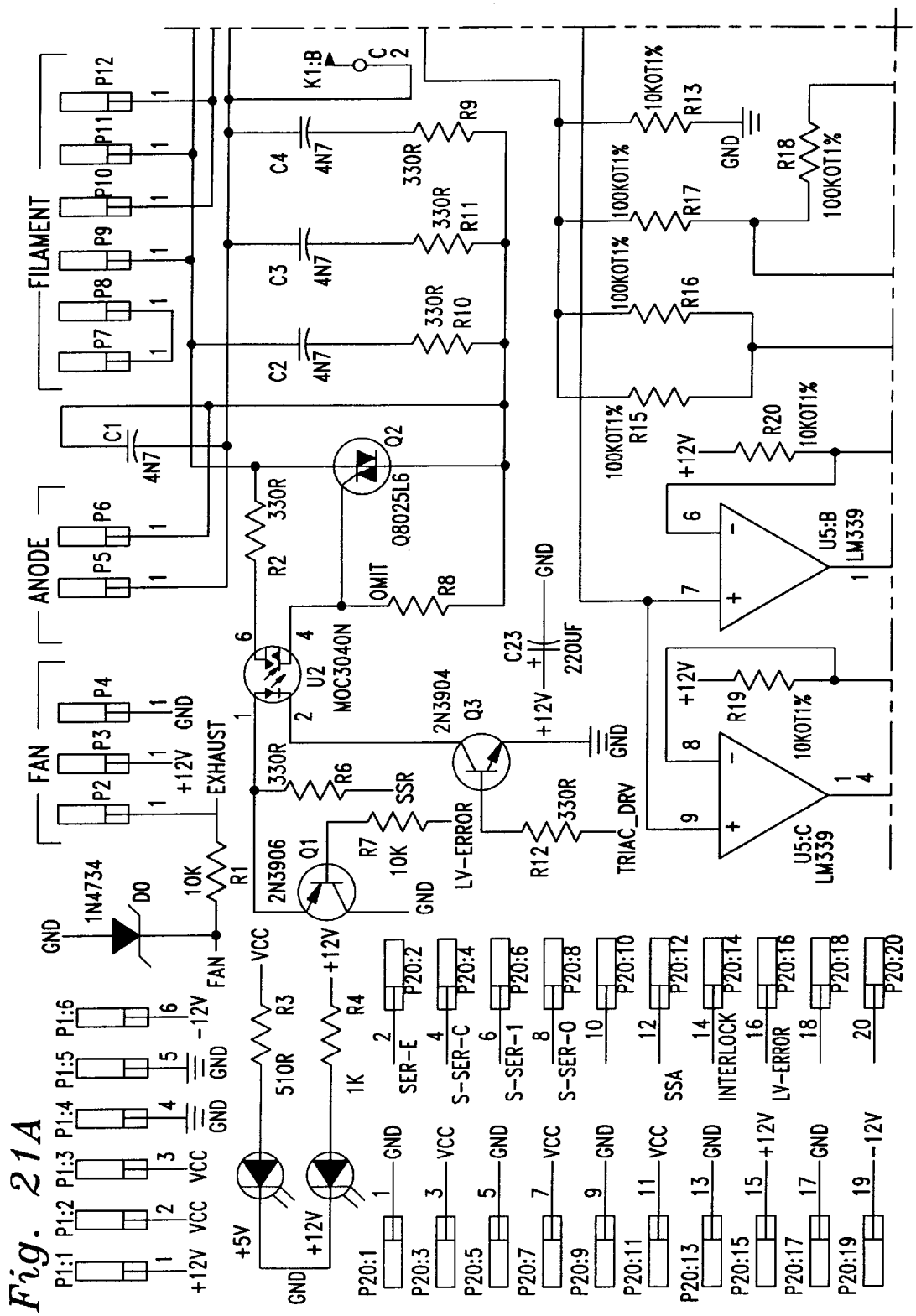
FIG. 21 is another schematic of the power control module shown in FIG. 6.
Figure 21B:
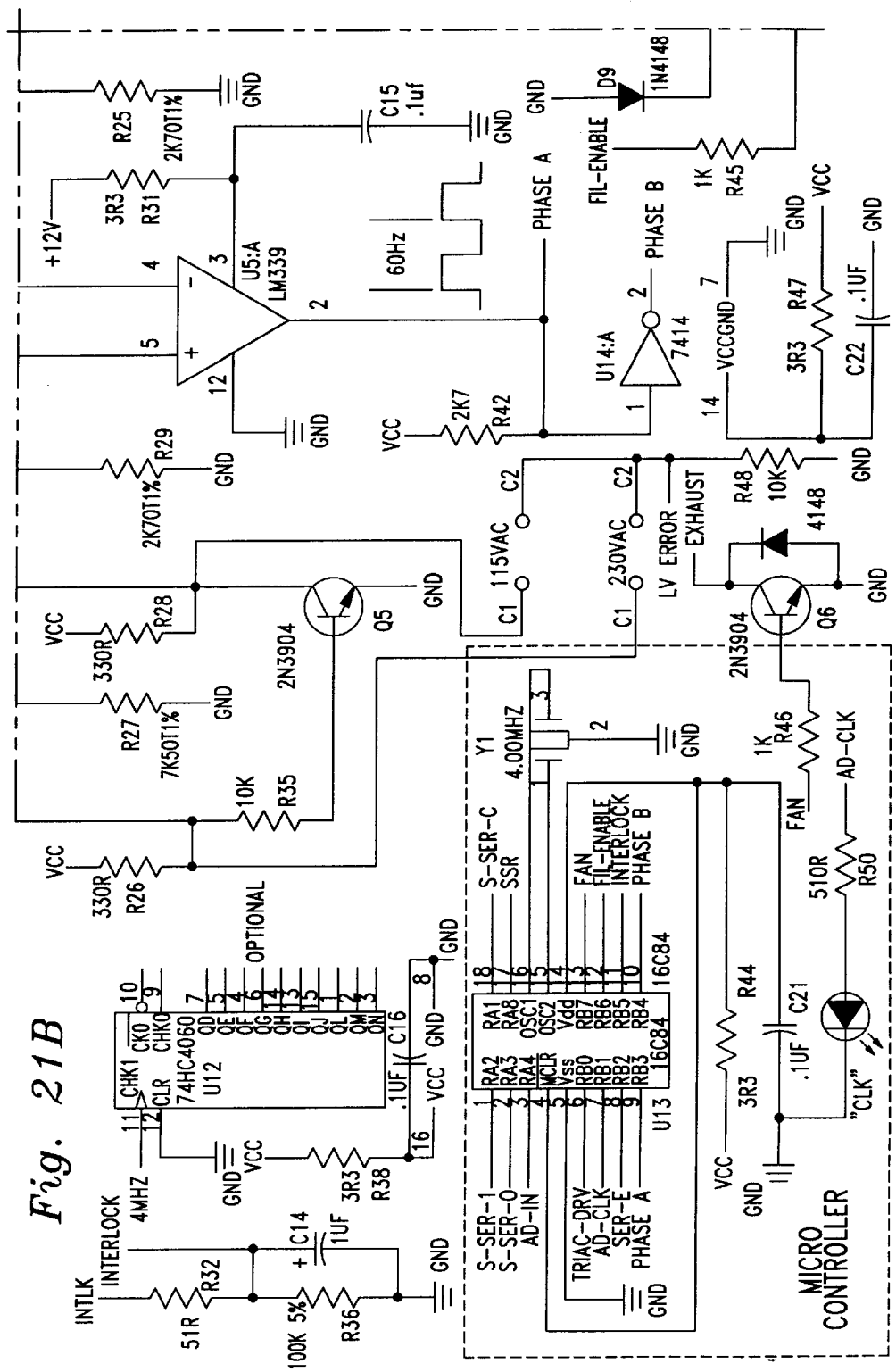
Figure 21C:
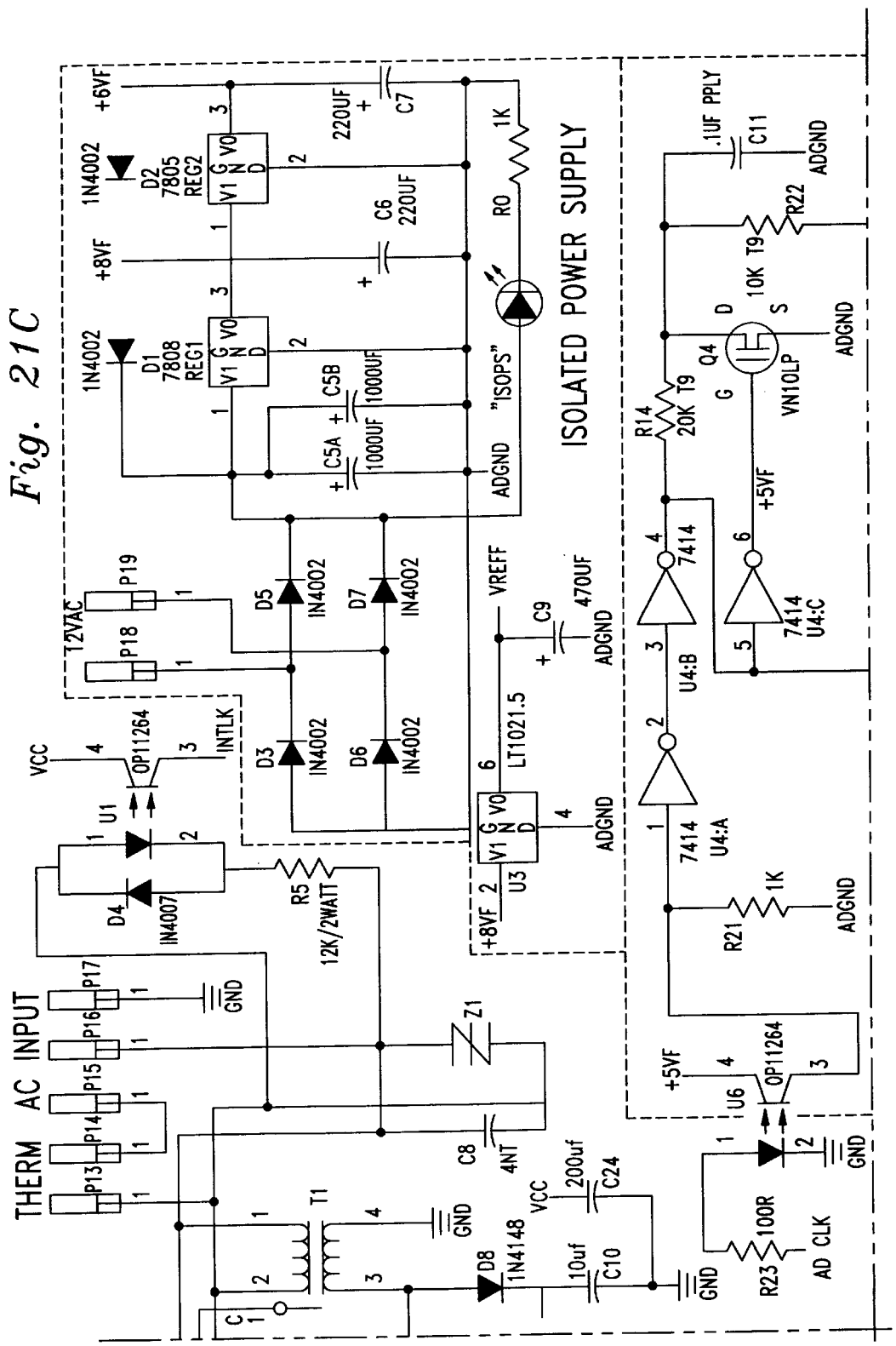
Figure 21D:
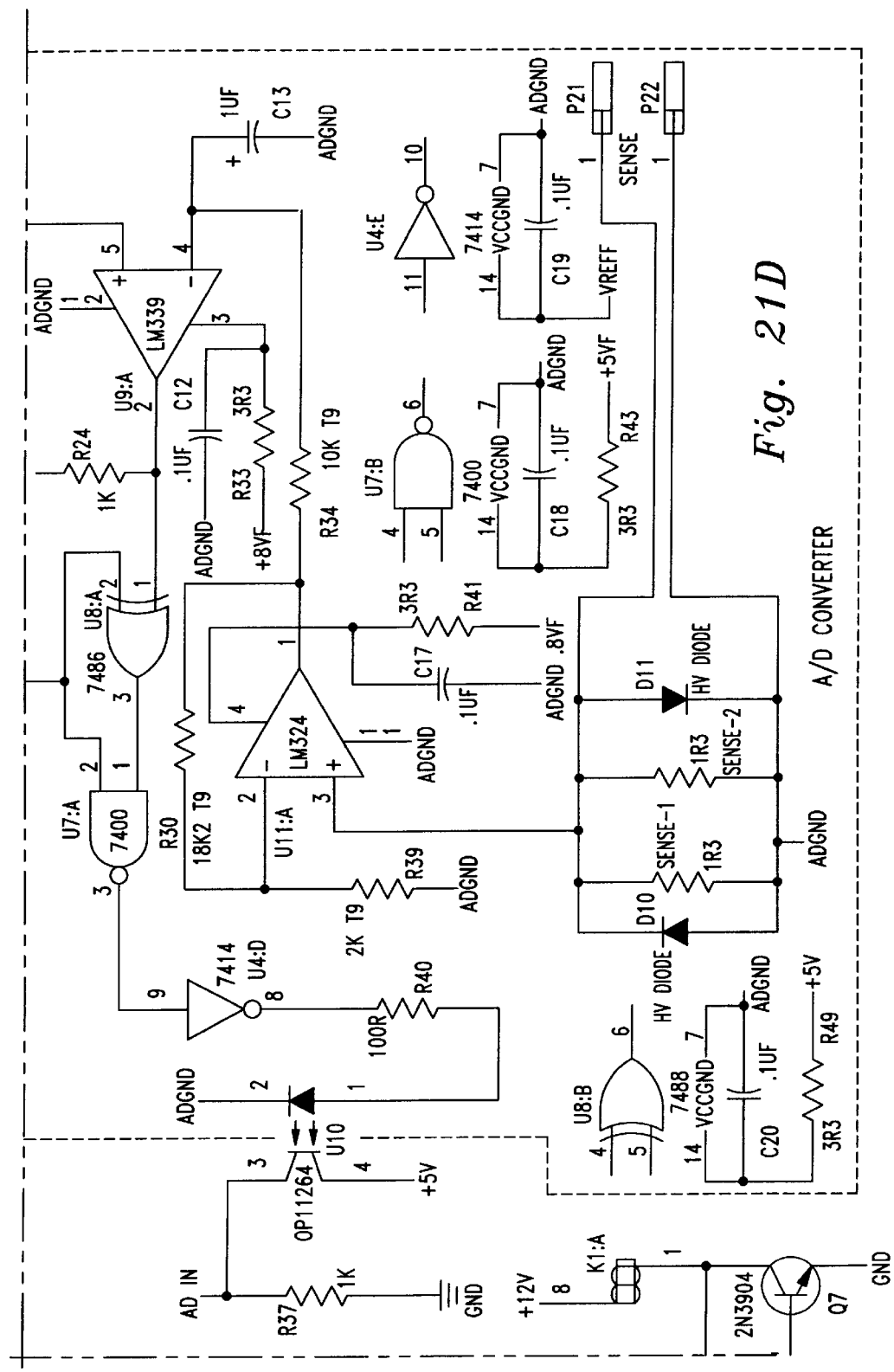

Referring to FIG. 19, the magnetron is operatively coupled to an outside wall of the base branch of the quadrature wave guide and communicates with the base branch of the quadrature wave guide via a magnetron antenna hole 220 disposed through a side wall of the base branch of the wave guide. In addition, a tuning or attenuating stub 222 extends through an outside wall and into the first branch 204 of the wave guide 200 at a location proximate the bifurcation of the wave guide into the first and second branches. The tuning stub 222 is dimensioned to attenuate a third energy mode such that there are only two substantial energy modes being delivered to the chamber. In other words, tuning stub filters out measureably a third mode, assuring only two modes enter the chamber at peak efficiency. The third module used to have a drastic effect on sample position tolerance and uniform drying.

Referring to FIGS. 20 and 21, two alternative component schematics are shown of a microwave phase controller according to the instant invention. The first microwave phase controller (FIG. 20) generally includes nine building blocks wherein one of the building blocks is a unique triac topology for controlling the average power output of a magnetron. The nine building blocks of the microwave phase controller include: a system power supply, a line synchronization detector, a discrete pulse width modulator, a micro-controller pulse width modulator, a triac module, a duty cycle monitor, a filament current detector, serial ports and an anode current monitor.

SYSTEM POWER SUPPLY:

The microwave phase controller employs a universal switching power supply to power the system. The outputs of the power supply are plus five volts, plus twelve volts and a negative twelve volts. The primary of the system power supply is fuse protected.

LINE SYNCHRONIZATION:

A common 50/60 hertz AC input is sampled by a small iron core transformer T1. The secondary S1 of the iron core transformer is referenced to ground and provides a signal which feeds into a comparator U1. The same signal is also rectified and filtered by diode D1 and capacitor C5 to provide a line amplitude regulated reference voltage with respect to the input AC amplitude. A pull up resistor R1 provides a TTL level conversion. The output of the comparator U1 is a crisp 60 hertz square wave. For microcontroller pulse width modulation the output signal of the comparator is fed directly into a processor or microcontroller U5 and it is also set to an inverter U3 to provide the complement for an opposite phase detection. A light emitting diode (LED1), a transistor Q2, resistors R7 and R9 make up a 60 hertz "sync" LED indicator drive. For the discrete pulse width modulation an exclusive OR gate U2, an inverter U3, a capacitor C7 and a resistor R11 make up a negative going edge frequency doubler. The combination of capacitor C7 and resistor R11 provide the desired pulse width of the doubler. Note that a 120 hertz frequency is needed to provide drive throughout both 60 hertz phases.

DISCRETE PULSE WIDTH MODULATOR:

The discrete pulse width modulator is designed around a 555 timer chip U7. The timer chip U7 receives a negative going 120 hertz signal from an inverter U3, negative because the 555 triggers on negative transitions. The pulse width of the 120 hertz signal is very narrow on purpose. The maximum duty cycle of the 555 chip output will be one hundred percent minus the "on time" of the 120 hertz pulse width. A power adjustment variable resistor VR1, a variable resistor VR2 and capacitor C8 create the RC time constant for the 555 delay. When the negative edge of the pulse is detected by the 555 chip, the output (pin 3) goes high, shutting drive off to a triac Q1 via the inversion of a 2N3906 transistor Q3. The 555 chip begins a delay between several micro-seconds and approximately eight milli-seconds. When the delay is over, the output (pin 3) of the 555 chip goes low turning on the triac Q1 until zero current flows through the triac Q1. The time between the "delay finish" and zero crossing of the phase is the duty cycle "on time". Adjusting the delay time smaller starts the triac Q1 earlier in the cycle delivering more average power to the load. Note that no power is delivered to the load until the processor U5 or PIC is turned on by pressing a start button and a filament current in a secondary of a filament transformer T2 is detected. At that time, a fixed thirty second timer begins allowing power to be delivered to the load for that time for a run which is after the triac drive relay K1 closes. An off button stops the delivery of power at any time.

MICRO-CONTROLLER PULSE WIDTH MODULATOR:

The micro-controller pulse width modulator replaces the discrete pulse width modulator and is designed around a PIC 16C84 micro-processor U5. Phase detection signals arrive at pins 1 and 2, 60 hertz square waves 180 degrees out of phase from each other. In the software of the instant invention, a delay is created after the rising edge of one of the phase signals is detected. This process is completed for both phases in the same manner. Note that the value of the delay is adjustable by accessing a look-up table in the software system. A down and an up bottom may be used to ask the software program to "bump" the delay value by selecting the past or next value in the look-up table. When the start button is pressed a filament enable line goes high driving a relay K2. This allows power to be delivered to the filament winding of the magnetron. If no filament current is detected, the triac drive relay K1 will not close allowing anode drive of the magnetron.

TRIAC MODULE:

The unique triac topology includes an optical coupler U6 for isolation and drive of a gate of the triac Q1. Pin 1 of the optical coupler U6 is pulled high with a 330 ohm resistor R16 and a low signal at pin 2 creates a drive signal for the triac. The triac Q1 is preferably a 800 volts, 25 amp isolated case device from Motorola. A one square-inch heat sync preferably provides moderate thermal dissipation for the device. A resistor R20 provides gate current when the optical coupler U6 turns on.

A snubber network is provided to provide protection to the triac from voltage spikes generated by the huge inductive load. The snubber is comprised of resistors R17, R18, R19 and capacitors C10, C11 and C12. A series power resistor R21 is added to increase the protection and lower the conducted admissions. Note that the triac is independently fused with fuse F2 which is rated at 10 amps.

DUTY CYCLE MONITOR:

A duty cycle monitor port may be provided for evaluation purposes. This duty cycle monitor port may be implemented by connecting an inverter to the optical isolator at pin 2 which will provide a positive going signal that can be integrated by a digital volt meter. A 10 kilohm potentiometer, VR3, is employed for scaling the signal. Preferably, it is adjusted so that a 1 volt reading on the digital volt meter is correlative to a one hundred percent duty cycle.

FILAMENT CURRENT DETECTOR:

The filament current of the magnetron is monitored by placing a secondary wire of the filament transformer through a current transformer torriod CT1. An output of the current transformer is rectified, filtered, and loaded by diode D3, capacitor C13 and resistor R29. As the amplitude exceeds 5 volts, a zener diode D2 starts to conduct turning on a transistor Q5. The transistor Q5 than pulls down a 10 kilohm transistor R26 thereby informing the processor U5 that current is following in the filament and the anode drive can be initiated. A light emitting diode, LED3, shows that current has been detected.

SERIAL PORT:

A serial port is preferably provided for software development purposes. This can be implemented by the use of a MAXIMUM 232IC delineated as U4 in the schematic.

ANODE CURRENT MONITOR:

The anode current can be monitored by placing a digital volt meter, for example a FLUKE 77 hand-held meter, in series with the multiplier high voltage diode. The hand-held meter is run in its current mode to take measurements. Protection against damage to the hand-held meter can include clamp diodes and neon bulbs.

Referring to FIG. 21, the second preferred embodiment of the microwave phase controller is designed to drive the microwave chamber. The concept of controlling the average output power of the magnetron with a TRIAC topology is proven. The microwave phase controller design is made up of six building blocks.

System power
Line sync detector
Micro-controller pulse width modulator
Line voltage detection
TRIAC module Isolated Anode current A/D Each of the building blocks will be discussed in detail.

SYSTEM POWER:

The system power is supplied by an off the shelf universal switching power supply. The outputs are +5 volts, +12 volts, and –12 volts. Primary is fuse protected.

LINE SYNC DETECTOR:

The 50/60 hz ac input is sampled by a small icon core transformer (T1). Referenced to earth ground, the signal is fed to a comparitor (U5). The same signal is also rectified and filtered (D8, C10) to provide a line amplitude "regulated" reference voltage with respect to the input ac amplitude. Pull up resistor (R42) provides the TTL level conversion. The output of the comparitor (U5) is a crisp 60 hz square wave. The signal is fed directly into the 16C84 processor (U13), it is also sent to an inverter (U14) to provide the complement for the opposite phase detection. This detection of the line frequency is necessary for TRIAC turn on timing, explained later.

MICRO-CONTROLLER PULSE WIDTH MODULATOR:

The micro-controller PWM is designed around a PIC 16C84 micro-processor (U13). Phase detection signals arrive at pins 9 and 10, 60 hz square waves 180° out of phase from each other. In software, a delay is created after the rising edge of one of the phase signals is detected (zero crossing point). This process is completed for both the phases in the same manner. The longer the delay value, the less average power delivered to the magnetron. The desired power level, is received via synchronous serial communication, from the digital board micro-processor (Z-180). This power level value is actually sent as desired Anode current A/D counts. The 16C84 matches the power level counts to the Anode current A/D counts received from the isolated A/D circuit, constantly adjusting the delay time from the phase signal zero crossing to when the TRIAC is turned on. This is the topology of regulation.

LINE VOLTAGE DETECTION:

Transformer (TI), diode (D8) and capacitor (C10) provide a filtered DC voltage that represents the input line voltage amplitude. An average voltage of about 3 vdc is recovered with an input voltage of 115 vac, and about 6 vdc for an input voltage of 230 vac. U5:B and U5:C are comparing a fixed reference voltage to the recovered input line voltage sample. The board can be configured for two different line voltages by selecting jumper "115VAC" or "230VAC". If the sampled line voltage does not match the selected configuration, the 16C84 will not allow the TRIAC to turn on, and the Z-180 receives the error message prompting the user that the configuration is mismatched.

TRIAC MODULE:

The TRIAC module consists of an optical coupler (U2) for isolation and drive of the TRIAC gate. Pin 1 is pulled high with a 330 ohm resistor (R6) only when the SSR "set system run" line is set high by the Z-180. The drive can be aborted if the line voltage status fails by turning on Q1. The TRIAC (Q2) is a 800 volt, 25 amp, isolated case device from Motorola. A 3 square inch heat sink provides moderate thermal dissipation for the device. R2 provides gate current when the opto-coupler turns on. The components that make up the snubber network are R9, R10, R11, C2, C3 and C4. These components provide protection to the TRIAC from voltage spikes generated by the huge inductive load. A series power resistor (0.5 ohm/55 watt) is added between the TRIAC and the Anode high voltage transformer to increase the protection and lower the conducted emissions. The TRIAC power source is independently fused at 10 amps.

ISOLATED ANODE CURRENT A/D:

The Anode current is necessary to monitor so the closed loop system can regulate the average power the magnetron delivers. The current that the Anode receives flows through the sense resistors "SENSE1, SENSE2". The voltage across the sense resistors represent the Anode current. At full power the recovered voltage across the sense resistors is about 160 mV. Should the sense resistors open up, a lethal potential (4200 v/0.25 amp) would be present at the isolated A/D circuit. To provide a measure of safety, two high voltage diodes (D10, D11) clamp across the sense resistors to hold the high voltage to a safe level of about +/–2 v. The A/D also is optically isolated by U6 and U10. This provides extra safety that the compliance agencies will require. After the voltage is recovered from the sense resistors, it is fed to an OP-AMP (U11:A) that boosts the signal to a more workable level (Gain—10). A ramp generator is made up of U4:A,B, C, C11, R14, U11:B and Q4 is the switch. Ramp clock is provided by the 16C84 (AD-CLK). The voltage reference IC (U3) provides a "perfect" voltage for U4 so the ramp generator does not drift with temperature. The ramp slope is compared to the amplified analog voltage at U9:A. The output of the comparitor (U9:A) stays high until the ramp slope matches the analog voltage amplitude, then the output switches low. If the analog voltage is low in amplitude, the comparitor switches low sooner. If the amplitude is higher, then the comparitor switch time is longer. Synchronizing the output of the comparitor with the A/D clock takes place at U8:A and U7:A. The output of U7:A is a pulse width modulator that operates at the A/D clock frequency with a pulse width that is proportional to the average current that flows across the sense resistors. In the 16C84 software, an 8 bit timer starts counting at the beginning of the pulse width received, and stops when the pulse goes away.

In use and operation, and referring to the drawings, the microwave moisture analyzer is a state of the art microprocessor based moisture/solids analyzer 10 which uses the principles of loss on drying (LOD) analysis. Samples are heated using microwave energy to liberate moisture or other volatiles while continuously weighing the sample with an integral precision electronic balance until end point conditions are met. When the analyzer is turned on by placing the on/off switch on the back of the analyzer into the on position, the analyzer will proceed through a self diagnostic routine and then display a stand-by screen on preferably a backlit liquid crystal display 70. Preferably, the liquid crystal display 70 is a dot addressable device which allows the analyzer to convey a rich variety of detailed information in plain English descriptive prompts, menus, or help messages. The set-up of the microwave moisture analyzer is accomplished by merely selecting the appropriate routine from the menu driven software displayed on the LCD display 70. Drying parameters are easily entered through the soft keys 72, 74, 76, 78 or the numeric keypad either by touching the corresponding number or entering the exact value with the numeric keys. Preferably, the LCD display 70 will conveniently illustrate all of the drying parameters including units, temperatures and end point selections. The memory associated with the central processing unit can be used to store drying procedures with meaningful alpha-numeric program names while the recall routine allows easy selection. The simplicity of the soft keys and the numeric keypads and the display prompts make routine operations near-effortless. The microwave moisture analyzer automatically calculates and documents results on its internal printer. Preferably, a choice of printouts provide either a simple result or a format including selection of operator name, analyzer I.D., program name and drying perimeters, and for true customization, a multi-line header. As mentioned, the microwave moisture analyzer features data storage and in addition has the ability to provide statistical evaluations of selected data.

More specifically, when the on/off switch on the back of the analyzer is placed into the on position the analyzer proceeds through a self diagnostic routine and then displays a stand-by screen to the user via the LCD display. A title line on the top of the stand-by screen identifies the specific screen displayed along with date and time. In addition, the bottom of the stand-by screen identifies four different options which may be selected via the associated soft keys disposed below each respective option. These options include a recall option, a set-up option, a data option and a paper feed option. When the soft key correlative to the set-up option is pressed a set-up screen will be displayed on the LCD which preferably includes seven menu driven choices. These seven menu driven choices can be either initiated via the numeric keypad or by using the directional arrow keys to scroll up and down the menu and then hitting the enter key to select the highlighted option. These seven options include a beeper option, a develop option, a security option, a calibrate option, a print-out option, a clock option and an output option. The bottom of the screen of the set-up display provides the user with an exit choice or a help choice which can be initiated by pressing the correlative soft key located directly there beneath. The beeper option allows the user to turn on or off a sound annunciation when either a key is pressed or when an end of test is discerned by the analyzer. The beeper screen incorporates a stand-by option displayed in the lower menu and can be used to go back to the stand-by screen by pressing the soft key associated therewith.

The second option of the set-up screen is preferably the develop option wherein drying procedures can be developed by optimizing the drying parameters for specific applications. Specifically, when the develop option is chosen a develop screen will be displayed with eight selections to choice from. The selections include units, power one, time one, power two, time two, slope, target and mode choices. Any one of these options may be initiated by either pressing the corresponding numeral on the numeric keypad which correlates to the option or by using the direction keys to scroll through the options and then hitting the enter key when the option which is desired is highlighted on the LCD screen display. The units option allows the user to select or change the units of measure depending on a specific application. Thus, when the units option is selected the display will change to the list of units available to the user which preferably includes five choices: a moisture choice, a solids choices, a volatiles choice, a MG/L choice and a weight choice. After a unit has been selected the display will return to the develop screen showing the new unit selected.

The power one option allows the user to set the power or temperature to be used during a first time period. When the power one option is selected from the develop screen a power one screen will be displayed allowing the user to chose a power level between the range one to one hundred percent of the rated power output to the microwave containment chamber. Once the power is selected the analyzer will once again display the develop screen to allow the user to make a subsequent choice if the time in which the magnetron will be driven to provide the power one option is chosen by selecting the time one option of the development screen. This option provides a pop-up menu which allows the user to select a range of time of preferably between 0.1 minute and sixty minutes. A second power level may be chosen when using a two-step drying method. The second power level works identically to the first power level wherein the power level is selected by the user via a pop-up menu. Likewise, a time two option of the development screen allows the time at which the second power level will be driven to by chosen by the user as has been delineated for the time one option. The next option on the develop screen is the slope option. The slope option is a function which provides an automatic end point to the test. The slope function consists of two variables, a window of time and a percent of initial weight (% IW) change. During the test, the weight loss of the sample is continuously monitored within the moving window of time. When the loss of weight within the window is less than the set percent of initial weight, the slope criteria has been met. The final weight is taken and the calculation is done to end the test. The time window correlative to the slope preferably has a range between one and sixty seconds. The user may return to the develop screen by simply pressing the enter key after entering the percentage of initial weight and/or a window of time or by simply turning off the slope completely.

The next option of a target option wherein the user can enter a target initial weight preferably in grams within a range of zero point one to thirty grams and then press the enter key to set the parameters.

The last option of the develop screen is a mode option wherein the user may select between a standard mode, a MG/L mode, a pre-dried pad mode or a syringe mode. Once the user has completed his development of the sample to be assayed he may simply use the save option displayed on the soft key menu by pressing the associated soft key. Once the save option has been initiated the user is allowed to select a location to store the develop program as a program number, for example one through ninety-nine. In addition, the user may specifically name the program via a pop-up program name showing the alphabet and various characters. The user uses the direction arrow keys to highlight the character on the pop-up menu and then presses and enter key to spell out the name of the program, this name is then saved using the soft menu save option. When the user has completed these functions the software will revert back to the standby screen wherein the soft menu includes a recall option, a set-up option, a data option and a paper feed option which may be initiated by activating any one of the soft keys associated therewith.

The set-up option includes a security option wherein the user can set up a security routine for precluding unauthorized personnel from using the analyzer. For example, the user can set up a specific password which must be entered prior to the analyzer being activated. This is done in the same manner as naming a program. In addition, the security menu includes option where programs can be cleared, data can be cleared, system information can be provided and programs can be alphabetized.

The set-up option also includes a calibration option wherein the precision balance can be calibrated. For example, once the calibrate option is displayed the user can place a predetermined amount of weight on the balance when prompted by the display and the analyzer will automatically recognize the weight and adjust the weight display to correspond thereto. For example, a fifty gram weight can be placed on the sample carriage when prompted by the display and will result in display a "calibration done" output on the LCD when the calibration has been successful.

The following outlines the typical steps used in developing an optimized drying procedure. In general, a standard convection oven method is the basis for beginning to develop a method on the analyzer. Sequentially, various parameters will be changed in order to meet specific methods development objectives. Note that steps 3–7 below do not need to be done in order, but rather as necessary. Finally, the procedure will be verified for accuracy across the range of moisture typical for the samples.

First, a typical sample with a known moisture value is chosen to do most of the methods development work. The method should then be verified and modified based on a larger sample set to improve method robustness.

DEVELOPMENT STEPS

1). Sample preparation
2). Duplicating the standard convection oven method
3). Selecting the presentation technique
4). Optimizing sample weight
5). Choosing a standby temperature
6). Selecting the optimum endpoint
7). Optimizing the drying temperature
8). Developing a two step drying procedure A sample preparation technique should be chosen to:

1). Provide a representative sample testing.
2). Allow rapid moisture loss.

Dry the sample at the same temperature as a standard oven method. Test results will be compared to the known value. Several replicates of the develop sample should be tested noting recovery, precision, sample appearance after testing and the time of analysis. Set the following drying parameters and begin testing:

1). Set Temp1 to the drying temperature of the standard method.
2). Use the default automatic slope endpoint setting (0.05%/1 min.).
3). Select the appropriate units.
4). Use a default standby temperature (60° C.).
5). Use approximately 10 grams of sample for testing.

If the sample material is a liquid or paste, a dispersing agent will be necessary. This will be noticeable if in step one the sample formed a crust during testing. The crust will prevent moisture from being liberated from the sample rapidly and likely cause a premature endpoint with the default slope setting.

A sample size should be chosen that is representative. However, a large sample size will increase the analysis time. At the same time, it may be necessary to get the desired reproducibility especially for low moisture samples.

The standby temperature is that which the heating chamber will equilibrate between tests. The default standby temperature is 60° C.

The reason to change the standby temperature is principally one of reducing analysis time.

The analyzer offers a variety of ways to end the analysis including time-out or automatic slope. The default value is the automatic slope with settings of 0.050%/1 minute.

The temperature which is chosen to dry the sample is based on the nature of the sample and the temperature which is needed to eliminate volatiles. Changing the drying temperature to a higher temperature can dramatically decrease the analysis time.

In some cases it may be advantageous to develop a two step drying procedure. This consists of two different drying temperatures for Temp 1 and Temp 2. One may go from a high temperature to a lower temperature, or from a low temperature to a higher temperature.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A moisture analyzer apparatus, comprising in combination:
    weighing means operatively disposed within a microwave chamber, said chamber having a cylindrical side wall, a base at one end of said cylindrical side wall and a top at another end of said cylindrical side wall, said apparatus receives a sample on said weighing means;
    and said microwave chamber receives microwave energy to dry said sample to determine moisture loss upon drying the specimen.

2. The apparatus of claim 1 including first and second magnetic modes, oriented transverse with respect to each other.

3. The apparatus of claim 2 including a wave guide leading to said microwave chamber, and a tuning stub in said wave guide to attenuate a third magnetic mode.

4. The apparatus of claim 1 including means for loading said sample from said top of said chamber.

5. The apparatus of claim 1 including tuning rods in said microwave chamber.

6. The apparatus of claim 1 including quartz pads located in said microwave chamber to receive a sample to be dried.

7. The apparatus of claim 1 including two canoe shaped portals passing through said base to admit microwave radiation into said microwave chamber.

8. The apparatus of claim 1 including a wave guide interposed between a magnetron and said microwave chamber, ducting radiation to said chamber, said wave guide being substantially Y shaped including a base wave guide fed by said magnetron and bifurcated into a first wave guide feed and a second wave guide feed at an intermediate junction, each said guide feed leading to its own portal in said base of said chamber, and each said portal provided with a tuning rod, said tuning rods separated from each other by an angle, and a tuning stub fixed in said wave guide to attenuate one magnetic mode.

9. The apparatus of claim 1 wherein said chamber is divided into an upper chamber and a lower chamber, each having cylindrical side walls of like diameter and oriented in registry,
    and hinge means between said upper and lower chamber allowing access to a sample receiving carriage of said weighing means by rotating said upper chamber about a pin defining an axis of rotation proximate to an exterior of said chamber, and a latch mechanism to hold said upper and lower chambers together,
    said upper and lower chambers guarded by switch means to disable a microwave magnetron during access to said carriage.

10. The apparatus of claim 9 including a choke operatively coupled between said upper and lower chambers.

11. The apparatus of claim 1 including a plurality of input means operatively coupled to said apparatus and a plurality of output means reflective of moisture analysis.

12. The apparatus of claim 11 wherein said input means is a plurality of keys and said output means includes a printer and a display.

13. A method for loss on drying, the step including:
    placing a specimen in a cylindrical chamber of a microwave;
    continuously weighing the specimen while powering the microwave to dry the specimen;
    venting moisture from the microwave during a first wave of drying, and sampling the weight change periodically.

14. The method of claim 13 further including the step of decreasing the microwave power during a last phase of the drying step.

15. The method of claim 13 including treating the specimen only with transverse magnetic modes $TM_{012}$ and $TM_{111}$.

16. The method of claim 15 including suppressing $TM_{012}$ with a tuning rod.

17. The method of claim 16 including attenuating a third energy mode with a tuning stub.

18. The method of claim 17 including disabling the microwave power when accessing the interior of the cylindrical chamber.

19. A microwave moisture analyzer; comprising in combination:
   a microwave containment chamber including a bottom wall, a top wall and a substantially cylindrical side wall extending between and connected to both said top and bottom walls, thereby defining a cylindrical chamber;
   said bottom wall including a pair of portals disposed therein;
   a microwave energy source;
   a wave guide operatively coupled between said microwave energy source and said pair of portals for delivering microwave energy to said cylindrical chamber;
   means for delivering only first and second magnetic modes, transverse to each other into said cylindrical chamber via said pair of portals;
   means for weighing a sample to be assayed; said weighing means operatively extending through said bottom wall and into said cylindrical chamber for supporting the sample to be assayed;
   means for controlling the delivery of microwave energy to said cylindrical chamber as a function of the sample being microwaved until said sample is dried; and
   means operatively coupled to said weighing means for automatically determining loss on drying moisture.

20. The analyzer of claim 19 including means for loading a sample from said top of said chamber.

21. The analyzer of claim 19 wherein said pair of portals are canoe shaped passing through said bottom wall to admit microwave radiation into said microwave chamber.

22. The analyzer of claim 19 wherein said wave guide is substantially Y shaped including a base wave guide fed by said microwave energy source and bifurcated into a first wave guide feed and a second wave guide feed at an intermediate junction, each said guide feed leading to its own portal in said bottom wall of said chamber, and each said portal provided with a tuning rod, said tuning rods separated from each other by an angle, and a tuning stub fixed in said wave guide to attenuate one magnetic mode.

23. The analyzer of claim 19 wherein said chamber is divided into an upper chamber and a lower chamber, each having cylindrical side walls of like diameter and oriented in registry,
   and hinge means between said upper and lower chamber allowing access to a sample receiving carriage of said weighing means by rotating said upper chamber about a pin defining an axis of rotation proximate to an exterior of said chamber, and a latch mechanism to hold said upper and lower chambers together,
   said upper and lower chambers guarded by switch means to disable a microwave magnetron during access to said carriage.

24. The analyzer of claim 23 including a choke operatively coupled between said upper and lower chambers.

25. The analyzer of claim 19 including a plurality of input means operatively coupled to said apparatus and a plurality of output means reflective of moisture analysis.

26. The analyzer of claim 25 wherein said input means is a plurality of keys and said output means includes a printer and a display.

27. A method for loss on drying, the step including:
   placing a specimen in a cylindrical microwave;
   continuously weighing the specimen while powering the microwave to dry the specimen;
   sampling the weight change periodically;
   treating the specimen only with transverse magnetic modes $TM_{012}$ and $TM_{111}$; and
   disabling the microwave power when accessing the interior of the cylindrical chamber.

* * * * *